US012630856B2

(12) United States Patent (10) Patent No.: US 12,630,856 B2
Czyz (45) Date of Patent: May 19, 2026

(54) IDENTIFICATION OF HOST-TARGETING MODULATORS OF BACTERIAL UPTAKE AND ASSAY FOR QUANTIFYING INTRACELLULAR BACTERIA

(71) Applicant: University of Florida Research Foundation, Incorporated, Gainesville, FL (US)

(72) Inventor: Daniel Czyz, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 855 days.

(21) Appl. No.: 17/904,386

(22) PCT Filed: Feb. 19, 2021

(86) PCT No.: PCT/US2021/018655
§ 371 (c)(1),
(2) Date: Aug. 17, 2022

(87) PCT Pub. No.: WO2021/168168
PCT Pub. Date: Aug. 26, 2021

(65) Prior Publication Data
US 2023/0074763 A1 Mar. 9, 2023

Related U.S. Application Data

(60) Provisional application No. 62/979,010, filed on Feb. 20, 2020.

(51) Int. Cl.
*G01N 33/50* (2006.01)
*C12Q 1/02* (2006.01)

(52) U.S. Cl.
CPC ......... *C12Q 1/025* (2013.01); *G01N 33/5091* (2013.01); *G01N 2469/10* (2013.01)

(58) Field of Classification Search
None
See application file for complete search history.

(56) References Cited

PUBLICATIONS

Eierhoff (PLoS Pathogen 2010 6:e1001099). (Year: 2010).*
International Search Report and Written Opinion for International Applciation No. PCT/US2021/018655, dated Jun. 28, 2021, (13 pages), United States Patent and Trademark Office, US.
Hazan, Ronen et al. "A Method For High Throughput Determination Of Viable Bacteria Cell Counts In 96-Well Plates," *BioMed Central Microbiology*, vol. 12, No. 259, pp. 1-7, Dec. 2012, available online: <URL: http://www.biomedcentral.com/1471-2180/12/259>.
Czyż, Daniel M. et al. "Host-Directed Antimicrobial Drugs With Broad-Spectrum Efficacy Against Intracellular Bacterial Pathogens," *mBio*, vol. 5, No. 4:e01534-14, pp. 1-14, Jul. 29, 2014, available online: <URL: https://journals.asm.org/doi/pdf/10.1128/mBio.01534-14>.
Stanley, Sarah A. et al. "Identification of Host-Targeted Small Molecules That Restrict Intracellular *Mycobacterium tuberculosis* Growth," *PLoS Pathogens*, vol. 10, No. 2: e1003946, pp. 1-16, Feb. 20, 2014, available online: <URL: https://doi.org/10.1371/journal.ppat.1003946>.

* cited by examiner

*Primary Examiner* — Changhwa J Cheu
(74) *Attorney, Agent, or Firm* — Alston & Bird LLP

(57) ABSTRACT

CFU-less assays of quantifying intracellular bacteria and methods of using the CFU-less assays to identify host-targeting modulators of pathogen uptake or killing by host cells are described. Also described are host-targeting modulators of pathogen uptake by host cells and methods of using the host-targeting modulators to treat infection

13 Claims, 21 Drawing Sheets

Starting number of bacteria $\propto 1/dT$

A
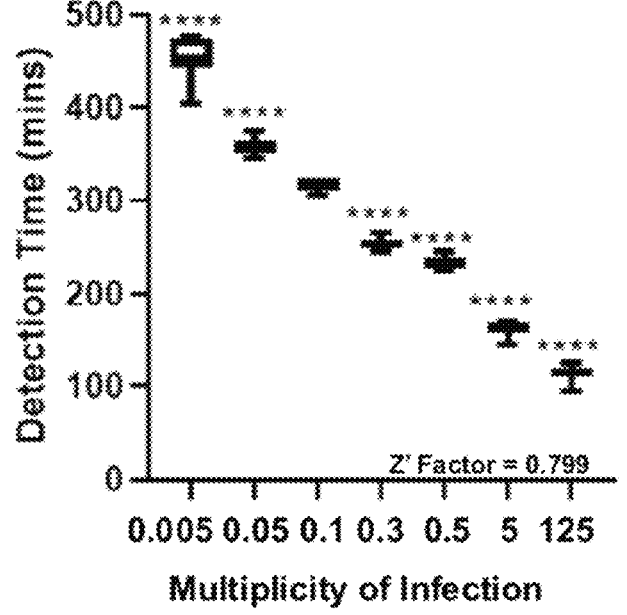
B. Average CFU/ml (log) MOI
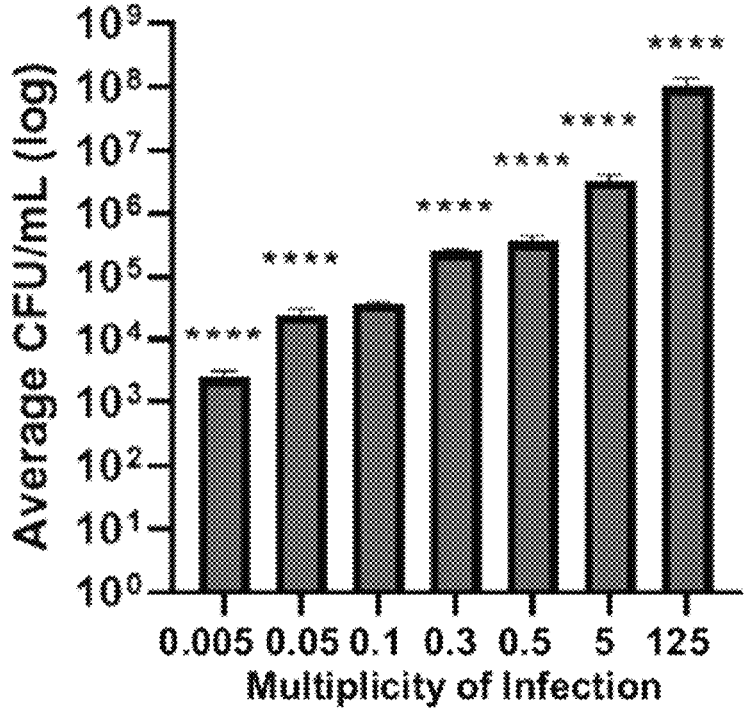
FIG. 17A-B

C. Titration

IDENTIFICATION OF HOST-TARGETING MODULATORS OF BACTERIAL UPTAKE AND ASSAY FOR QUANTIFYING INTRACELLULAR BACTERIA

CROSS-REFERENCE TO RELATED APPLICATIONS

This application is a national phase filing of International Application No. PCT/US2021/018655, filed Feb. 19, 2021, which claims the benefit of U.S. Provisional Application No. 62/979,010, filed Feb. 20, 2020, the content of each which is incorporated herein by reference.

INTRODUCTION

Antimicrobial resistance (AMR) is a growing problem. Currently, worldwide, infectious diseases remain the leading cause of death. Annually, about 2 million people develop hospital-acquired infections in the US alone and about 100,000 people die each year from infectious disease, and an estimated 35,000 deaths are directly related to AMR.

Bacteria have developed resistance to every class of antibiotics. Increases in current resistance, emergence of new resistance, and decreases in the development of novel antibiotics driven by the lack of targets and unfavorable economics of acute therapy drugs all increase the problem of antibiotic resistance.

The stagnation of antibiotic development and the dramatic rise in antibiotic resistance has created a gap in the availability of effective antimicrobials. Antibiotic resistance claims nearly 36,000 lives in the United States each year. It is estimated that by 2050 this number will increase tenfold.

Thus, there is a need to develop alternative therapies against antibiotic-resistant infections.

SUMMARY

Described are methods of analyzing drugs and other molecules for their ability to inhibit or treat infection by targeting a host cell. The described methods can be used to identify previously unknown anti-infective properties of existing drugs or other chemical and biological species. Identifying new uses for existing drugs can potentially lower the cost and speed the development of new therapeutics. Targeting the host rather than the pathogen may circumvent antibiotic resistance.

In some embodiments, methods of enhancing uptake of pathogenic bacteria by macrophages are described, the methods comprising contacting the macrophages with one or more compounds selected from the list consisting of: thiamylal, amlexanox, cefaclor, floxuridine, miltefosine, mitoxantrone, loperamide, doramectin, aminacrine, mebeverine, aminohippuric acid, fipexide, heptaminol, nicergoline, and menthyl benzoate. In some embodiments, the compounds are used to treat infection. In some embodiments, the compounds are used to treat infection by extracellular bacteria. In some embodiments, the compounds are used to treat antibiotic-resistant infection. In some embodiments, the compounds are used to treat antibiotic resistant infection by extracellular bacteria.

In some embodiments, are methods of inhibiting uptake of pathogenic bacteria by host cells are described, the methods comprising contacting the host cells with one or more compounds selected from the list consisting of: cefotetan, colistimethate, colistin, gentian violet, polymyxin B, berbamine, 7,2'-dimethoxyflavone, dehydroabietamide, fluticasone, gambogic acid, chlorquinaldol, anthothecol, quinacrine, cepharanthine, mitomycin, sanguinarium, triflupromazine, cysteamine, tenatoprazole, tilorone, methionine sulfoximine, cypermethrin, temazepam, and derivatives thereof. In some embodiments, the compounds are used to treat infection. In some embodiments, the compounds are used to treat infection by intracellular bacteria. In some embodiments, the compounds are used to treat antibiotic-resistant infection. In some embodiments, the compounds are used to treat antibiotic-resistant infection by intracellular bacteria.

Described are methods of treatment of antibiotic-resistant infection comprising administering to a subject a compound that modulates uptake of infectious pathogens by host cells. For infection by extracellular bacteria, the method comprises administering to a subject a compound that enhances uptake of the bacteria by host cells, such as macrophages. For infection by an intracellular bacteria, the method comprises administering to a subject a compound that inhibits uptake of the bacteria by host cells. The compounds can be identifying used the methods described herein. In some embodiments, the compounds are selected from the compounds of Tables 1 and 2.

In some embodiments, methods for analyzing intracellular pathogens, such as bacteria, and identifying compounds that modulate (enhance or suppress) host cell-mediated uptake of the pathogens are described. The methods provide for quantification of intracellular bacteria using colony forming units (CFU)-less assay (CLA). The methods can be used for quantifying bacteria internalized by a host cell or bacteria that remain viable after internalization by a host cell without the need to measure colony forming units. The described methods can also be used to assess growth of bacteria in axenic culture. Quantifying intracellular bacteria can be used to analyze modulation of bacterial entry into host cells and to assess efficiency of killing of a pathogen by macrophages. Quantifying intracellular bacteria can also be used to analyze exogenous therapeutic species, such as small molecules or biologics. This information can then be used to analyze or identify host-targeting mechanisms and/or compounds that modulate pathogen entry into host cells and/or enhance pathogen killing. Compounds identified using the described methods that modulate bacterial entry into host cells may be suitable for use against antibiotic-resistant bacteria. For extracellular bacteria, i.e., bacteria known for their extracellular growth and survival, enhancing uptake into host cells, e.g., macrophages, is expected to increase the clearance of infection. The methods can be used to identify compounds that increase uptake of extracellular bacteria by macrophages. Inhibiting bacterial uptake is expected to attenuate infections by intracellular bacteria, i.e., bacteria known for their intracellular growth and survival. The methods can be used to identify compounds that decrease uptake of intracellular bacteria by host cells.

CFU-less methods of measuring bacterial growth in axenic culture are described. The methods comprise, expressing in the bacteria a fluorescent protein, growing the bacteria in axenic culture, measuring fluorescence in the culture at regular intervals, and determining the earliest detection time, dT, a point at which the measured fluorescence value of the sample begins to increase. The methods can be used to determine the effect of compounds on the growth and proliferation of the bacteria. The methods can also be used to quantitate the number of bacteria in a sample by comparing the dT determined from the sample with dT values obtained from a standard curve generated for a range of known CFUs of the bacteria in axenic culture. Compounds identified using the described methods that modulate bacterial growth may be suitable for use against antibiotic-resistant bacteria.

BRIEF DESCRIPTION OF THE FIGURES

FIG. 17A-B. Graphs illustrating (A) Titration of MOIs using detection time (dT) (fluorescence) (B) Titration of MOIs using colony forming units to confirm the CLA method.

and graph illustrating detection time and identification of drugs that suppress and enhance uptake of *E. coli* by macrophages (right panel).

Figure 19:
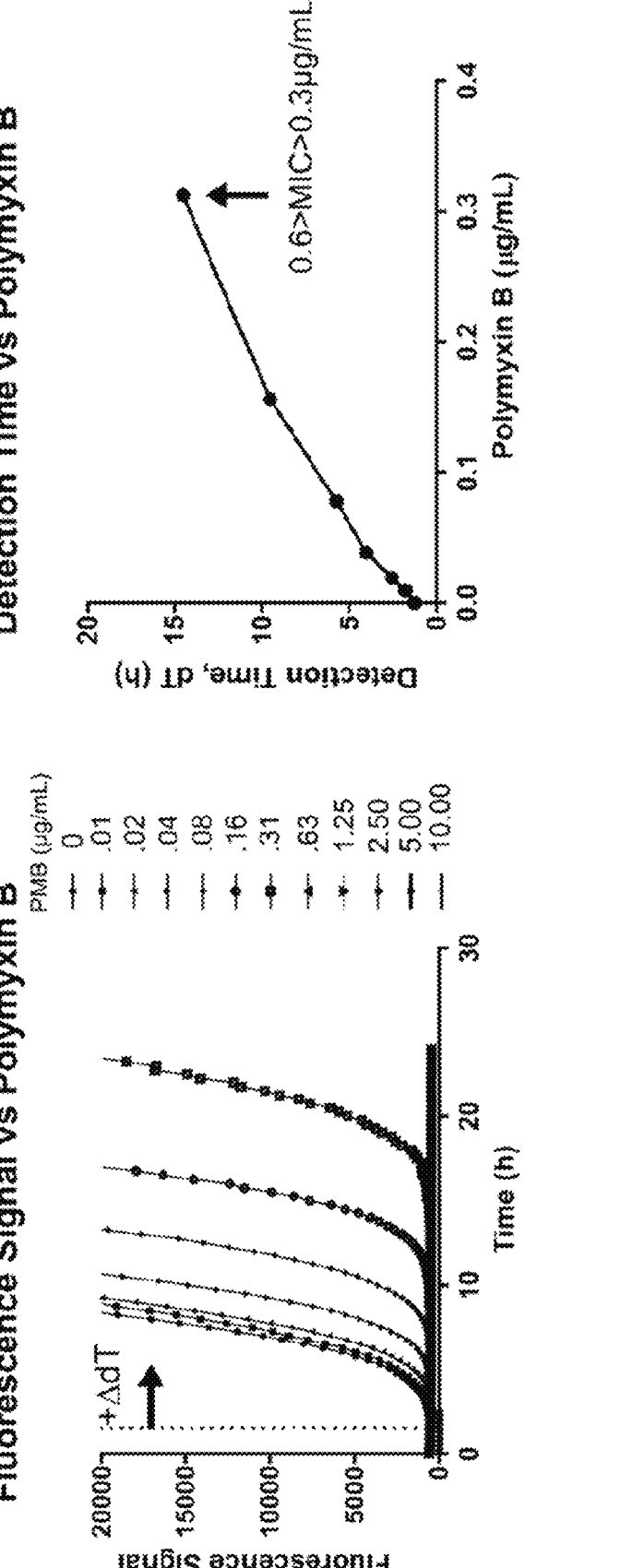

FIG. 19. Graph illustrating CFU-less assay to detect inhibition of gram-negative bacterial growth in axenic culture in samples treated with varying amounts of polymyxin B.

Figure 20:
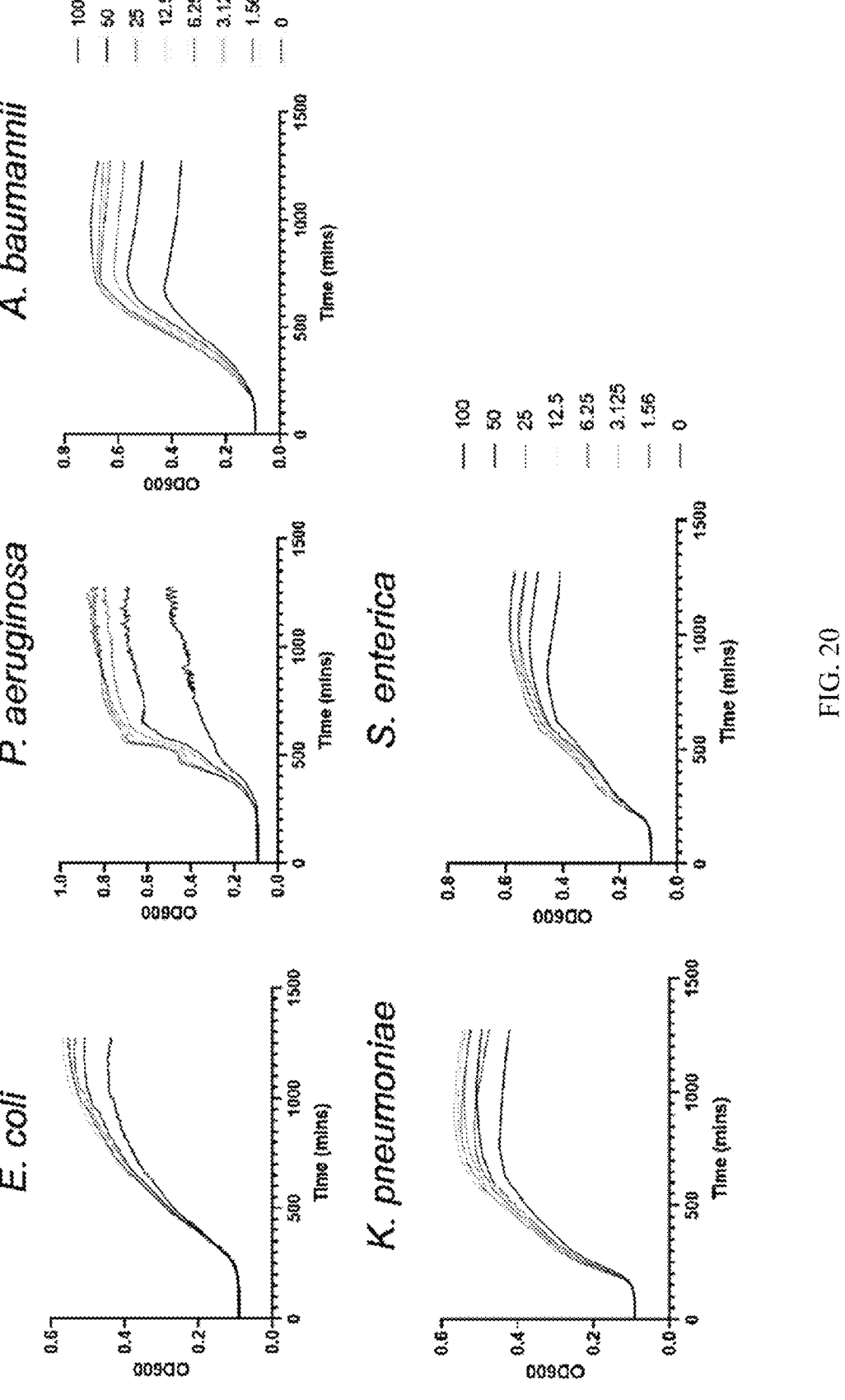

FIG. 20. Graphs illustrating axenic growth of gram-negative bacteria in the presence of one of quinacrine, one of the inhibitors as assessed by measuring optical density.

Figure 21:
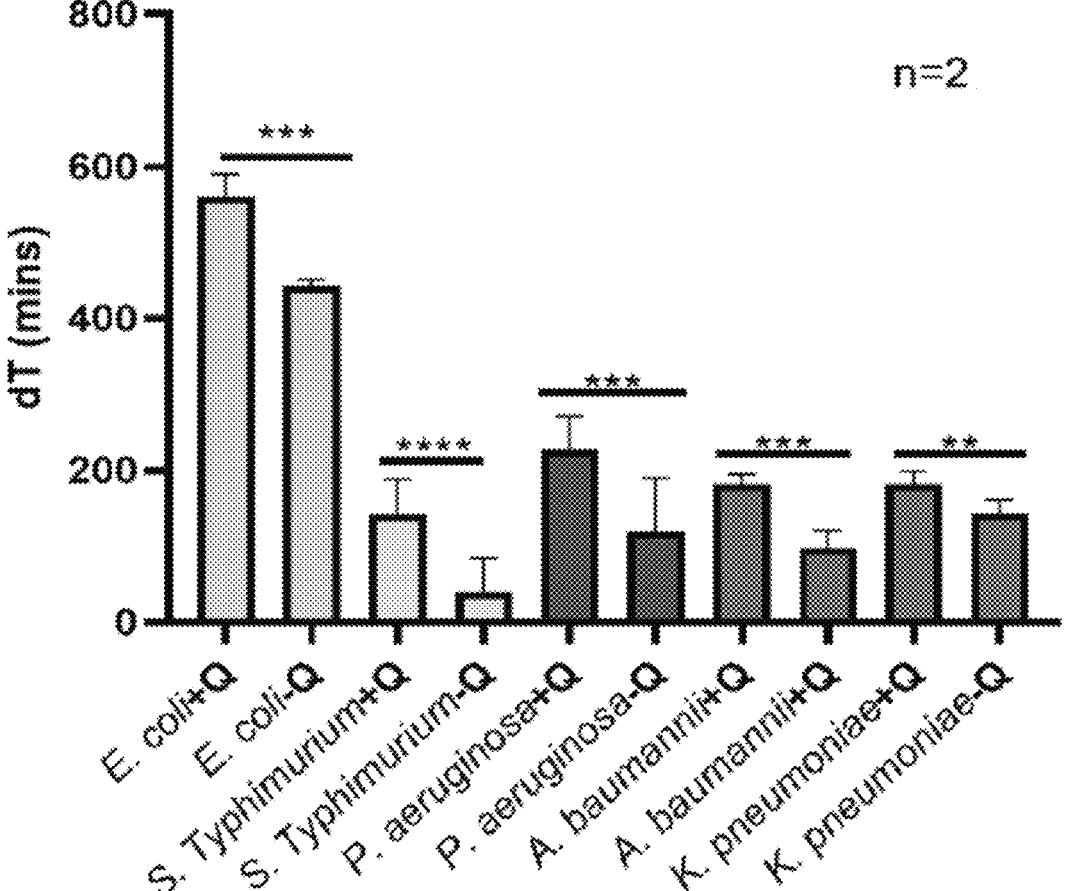

FIG. 21. Graph illustrating inhibitory effect (increased dT) on uptake of both intracellular and extracellular bacterial strains in RAW 264.7 macrophages treated with quinacrine.

Figure 22:
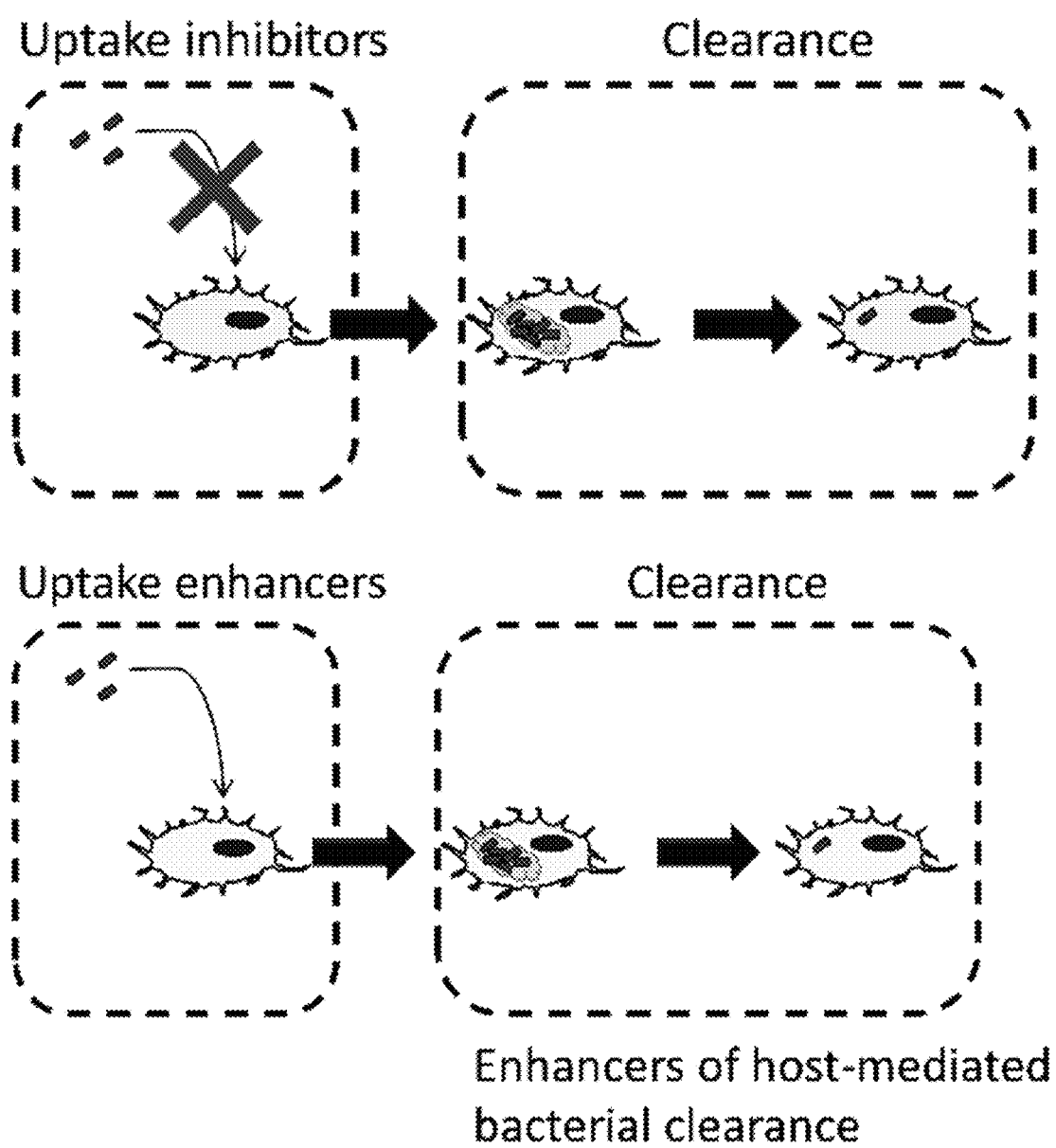

FIG. 22. Drawings illustrating host-targeted therapeutics inhibiting (top panel) or enhancing (bottom panel) uptake of the pathogen by the host cell.

DETAILED DESCRIPTION

I. Definitions

A "pathogen" is an organism that can cause a disease or illness in a host or host cell. A pathogen can be, but is not limited to, a virus, a bacterium, a protozoan, or a fungus. Pathogens cause illness to their hosts through a variety of ways. Pathogens can cause illness through direct damage of tissues or cells such as during pathogen replication, through production of toxins, and through induction of immune response against the pathogen by the host. A pathogenic bacterium can be a gram-positive bacterium or a gram-negative bacterium.

"Extracellular bacteria" are bacterial pathogens do not typically invade cells. Extracellular bacteria survive and proliferate in the extracellular environment. Extracellular bacteria do not typically survive in professional phagocytic cells (e.g., neutrophils, monocytes and macrophages). Extracellular bacteria include, but are not limited to, *Enterococcus* spp. (e.g., *Enterococcus faecium*), *Klebsiella* spp. (e.g., *Klebsiella pneumoniae*), *Acinetobacter* spp. (e.g., *Acinetobacter baumannii*), *Pseudomonas* spp. (e.g., *Pseudomonas aeruginosa*), and *Enterobacter* spp. Although these bacteria are commonly regarded as being extracellular, there are instances where they can persist inside of professional phagocytic cells.

"Intracellular bacteria" are bacterial pathogens typically invade cells. Intracellular bacteria are capable of surviving and proliferating inside host cells. Some intracellular bacteria can survive and proliferate in professional phagocytic cells. Intracellular bacteria include obligate intracellular pathogens and facultative intracellular pathogens. Obligate intracellular bacteria need a host cell to reproduce. Facultative intracellular bacteria are capable of living and reproducing in or outside of host cells. Obligate intracellular bacteria include, but are not limited to: *Chlamydia* spp., *Rickettsia* spp., *Coxiella* spp. (e.g., *Coxiella burnetii*), and certain *Mycobacteria* spp. (e.g., *Mycobacterium leprae, Mycobacterium tuberculosis*). Facultative intracellular bacteria include, but are not limited to: *Bartonella henselae, Francisella tularensis, Listeria monocytogenes, Salmonella* spp. (e.g., *Salmonella Typhi*), *Brucella* spp., *Legionella* spp. (e.g., *Legionella pneumophila*), certain *Nocardia* spp., *Neisseria* spp. (e.g., *Neisseria gonorrhoeae*), *Rhodococcus equi, Yersinia* spp., and *Staphylococcus* spp. (e.g., *S. aureus*.

A "label" or "detectable label" is a moiety or compound that can be detected and which can be produced by a pathogen. Labels can be proteins such as luciferase, fluorescent proteins, and enzymes. A pathogen can be transformed with a nucleic acid sequence encoding the label.

A "host cell" is a cell of the host which is either a target of infection by the pathogen or a professional phagocytic cell. A host cell can be a mammalian cell. A host cell can be a primary cell or an immortalized cell. A mammalian cell can be, but is not limited to, a human cell, or a mouse of other model organism cell.

"Professional phagocytic cells" or "professional phagocytes" include monocytes, macrophages, neutrophils, and macrophage-like cells.

A "host-targeting therapeutic" or "host-targeted therapeutic" is a drug or molecule that modulates a host cell and enhances or suppresses uptake or killing of a pathogen by the host cell. The host-targeting therapeutic can modulate uptake of the pathogen by one or more cells of the subject, enhance the ability of one or more cells of the subject to kill the pathogen, and/or target host resources and/or signaling pathways essential for intracellular survival and/or replication of the pathogen.

A "CFU-less assay" is an assay that can be used to quantify the number or amount of viable pathogen, such as bacteria, in a sample without determining the number of colony-forming units in the sample.

II. Methods of Identifying Modulators of Pathogen Uptake by Host Cells.

In some embodiments, methods for analyzing intracellular pathogens and/or identifying compounds that enhance or suppress host cell-mediated uptake of the pathogens are described.

In some embodiments, the methods comprise:

(a) labeling a pathogen with a detectable marker;

(b) incubating a host cell with a compound or interest;

(c) contacting the host cell with the labeled pathogen and incubating for a predetermined time; and (d) determining the amount of pathogen internalized by the host cell.

In some embodiments, the methods comprise:

(a) labeling a pathogen, such as a bacterium, with a detectable marker;

(b) obtaining host cells, such as macrophages;

(c) incubating a sample containing the host cells with one or more compounds of interest; optionally incubating the compound(s) with the host cells for sufficient time to allow the compound(s) to bind to the host cells or to affect one or more cellular processes of the host cells;

(d) optionally washing the host cells to remove compound(s) not associated with the host cells;

(e) adding the labeled pathogens to the sample and incubating for a period of time sufficient for the labeled pathogens to bind to, enter, or infect the host cells;

(f) washing the host cells to remove pathogens that are not bound to or internalized by the host cells and optionally adding an antibiotic that is toxic to the pathogen and does not enter the host cells to kill extracellular pathogen;

(g) lysing the host cells and collecting a sample of the lysate; and (h) determining the amount of pathogen internalized by the host cells by measuring the amount of pathogen and/or label in the lysate sample.

In some embodiments, the methods comprise:

(a) expressing a fluorescent protein in bacteria;

(b) optionally administering one or more compounds of interest to a test animal;

(c) contacting the animal model with the bacteria expressing the fluorescent protein;

(d) collecting one or more tissues, tissue cells, cells, or fluids from the animal model;

(e) optionally lysing the tissue cells or cells (f) determining the amount of pathogen in the tissues or cells from the animal model by measuring the fluorescent protein in the tissues, tissue cells, cells, or fluids.

The animal model can be, but is not limited to, a rodent (e.g., a mouse, a rat, or a ferret). The one or more compounds of interest can be administered to the animal model prior to, or after, contacting the animal model with the bacteria. Contacting the animal model with the bacteria includes, but is not limited to, infecting the animal with the bacteria, injecting the animal with the bacteria, contacting the animal with the bacteria, oral administration, gavage, sublingual administration, buccal administration, ocular administration, rectal administration, vaginal administration, otic administration, intranasal administration, inhalation administration, or topical administration. Injecting the animal with the bacteria includes, but is not limited to, intravascular injection, intravenous injection, intraarterial injection, intraperitoneal injection, intrathecal injection, tissue injection, intramuscular injection, or subcutaneous injection. The methods can be used to analyze infection in animal models, trace movement of the bacteria in animal models, or analyze whether a treatment, such as administration of the compound, alters bacteria replication or survival in, or migration to, various tissues, tissue cells, cells, or fluids in the animal model. Measuring the fluorescent protein in the tissues or cells includes, but is not limited to, direct measurement of fluorescence and performing a CFU-less assay as described herein. In some embodiments, the pathogen is a bacterial pathogen. The bacterial pathogen can be, but is not limited to: an *Acinetobacter* spp., a *Bartonella* spp., a *Brucella* spp., a *Campylobacter* spp., a *Chlamydia* spp., a *Clostridium* spp., a *Corynebacterium* spp. a *Coxiella* spp., an *Enterococcus* spp., an *Enterobacter* spp., an *Escherichia* spp., a *Francisella* spp., a *Klebsiella* spp., a *Legionella* spp., a *Listeria* spp., a *Mycobacterium* spp., a *Neisseria* spp., a *Nocardia* spp., a *Pseudomonas* spp., a *Rhodococcus* spp., a *Rickettsia* spp., a *Salmonella* spp., a *Shigella* spp., a *Staphylococcus* spp., a *Streptococcus* spp., a *Treponema* spp., and a *Yersinia* spp.

The pathogen can be labeled using methods known in the art. In some embodiments, labeling the pathogen with a detectable marker comprises inserting an expressible gene encoding a fluorescent protein into the pathogen. In some embodiments, pathogenic bacteria are labeled by expressing a fluorescent protein in the bacteria. The fluorescent protein can be expressed from a plasmid or other expression vector present in the bacteria or the fluorescent protein can be expressed from a gene that is integrated into the genome of the bacteria. The bacteria can be transformed with nucleic acid, such as a plasmid, encoding the fluorescent protein or infected with a viral vector encoding the fluorescent protein. The fluorescent protein can be, but is not limited to, a green fluorescent protein, a blue fluorescent protein, a cyan fluorescent protein, a yellow fluorescent protein, an orange fluorescent protein, or a red fluorescent protein, or a derivative thereof.

The fluorescent protein can be, but is not limited to Green fluorescent protein (GFP), GFP-like proteins, modified GFPs, GFP derivatives, eGFP, eqFP611, Dronpa, TagRFPs, KFP, EosFP/IrisFP, Dendra, mVenus, mCherry, emerald GFP, superfolder GFP, Azami Green GFP, TagGFP, Turbo GFP, AcGFP, ZsGreen GFP, T-sapphire GFP, blue fluorescent protein, EBFP, EGFP2, Azurite BFP, mTagBFP, Cyan fluorescent protein (CFP), SCFP, mECFP, Cerulean CFP, mTurquoise CFP, CyPET CFP, AmCyanl CFP, Modori-Ishi Cyan CFP, TabCFP, mTFP (Teal), yellow fluorescent protein (YFP), Topax YFP, Venus YFP, mCitrine YFP, YPet YFP, TagYFP, PhiYFP, ZsYellow YFP, mBanana YFP, orange fluorescent protein (OFP), Kusabira Orange OFP, Kusabira Orange2 OFP, mOrange OFP, mOragne2 OFP, dTomato OFP, dTomato-Tandem OFP, TagRFP OFP, TagRFP-T OFP, DsRed OFP, DsRed2 OFP, DsRed-Express (T1) OFP, DsRed-Monomer OFP, mTangerine OFP, Red fluorescent protein (RFP), mRuby RFP, mApple RFP, mStrawberry RFP, AsRed2 RFP, mRFP1 RFP, JRed RFP, mCherry RFP, HcRedl RFP, mRaspberry RFP, dKeima-Tandem RFP, HcRed-Tandem RFP, mPlum RFP, and AQ143 RFP.

In some embodiments, the host cell is a professional phagocytic cell (phagocyte). In some embodiments, the host cell is a cell or cell type that is normally infected by the pathogen.

The professional phagocytic cell can be, but is not limited to, a neutrophil, a monocyte, a macrophage or a macrophage-like cell. In some embodiments, the host cell is a primary macrophage. A primary macrophage can be, but is not limited to, a monocyte-derived macrophage (MDM) or a bone marrow-derived macrophage (BMDM). In some embodiments, the macrophage or macrophage-like cell is an immortalized cell or from an established cell line (a culture cell). The immortalized cell can be, but is not limited to, a THP1 cell, a RAW264.7 cell, an MV-4-11 cell, or a KG-1 cell. The cells can be from any host species, including, but not limited to, human and mouse.

In some embodiments, the host cell is a non-professional phagocytic cell normally infected by the pathogen. The non-professional phagocytic cell can be a primary cell or an immortalized cell (e.g., culture cell). As an example, *Mycobacterium leprae* exhibit tropism for Schwann cells and *Bartonella henselae* infect endothelial cells.

Host cells are incubated with one or more compounds of interest. For testing of multiple compounds, the host cells can be incubated with the compounds of interest in multiwell plates. The host cells can be incubated the compound(s) for a sufficient time to allow the compound(s) to bind to the host cells or to affect one or more cellular processes of the host cells. In some embodiments, the host cells are incubated the compound(s) for 0-24 hours, 0 minutes, less than 1 minutes, about 1 minute, about 2 minutes, about 3 minutes, about 4 minutes, about 5 minutes, about 10 minutes, about 15 minutes, about 20 minutes, about 30 minutes, about 40 minutes, about 50 minutes, about 60 minutes, about 75 minutes, about 90 minutes, about 105 minutes, about 120 minutes, about 150 minutes, about 180 minutes, about 4 hours, about 5 hours, about 6 hours, about 7 hours, about 7 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours before contacting the host cells with the pathogen. The pathogens can be added to the host cells in the presence of the compound(s) (i.e., without washing) or the pathogens can be added to the host cells after host cells are washed to remove compound not associated with the host cells.

The host cells are contacted with the labeled pathogen either concurrent with or subsequent to incubation of the host cells in the presence of the compound(s) of interest. The host cells are incubated with the labeled pathogen for a period of time sufficient for the labeled pathogens to bind to, enter, or infect the host cells. The host cells can be incubated with the labeled pathogens for about 15 to about 240 minutes, about 15 minutes, about 20 minutes, about 25 minutes, about 30 minutes, about 35 minutes, about 40 minutes, about 45 minutes, about 50 minutes, about 60 minutes, about 75 minutes, about 90 minutes, about 105 minutes, about 120 minutes, about 150 minutes, about 180 minutes or about 240 minutes. The pathogen can be added to the host cells at a multiplicity of infection (MOI) of about 0.005-125, about 0.005, about 0.05, about 0.1, about 0.2, about 0.3, about 0.4, about 0.5, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, or about 125. For some host cells or pathogens, an MOI greater than 125 may be required. MOI is selected based on the pathogen and the host cell and can be empirically determined.

In some embodiments, the host cells are washed after incubation with the pathogens. Washing can be performed to remove pathogens that are not bound to or internalized by the host cells. In some embodiments, the host cells are treated with an antibiotic that is toxic to the pathogen and does not enter the host cells. The host cells are treated with the antibiotic for a period of time sufficient to kill pathogen that has not been taken up (internalized) by the host cells. The host cells can be incubated with the antibiotic for about 15 to about 180 minutes, about 15 minutes, about 20 minutes, about 25 minutes, about 30 minutes, about 35 minutes, about 40 minutes, about 45 minutes, about 50 minutes, about 60 minutes, about 75 minutes, about 90 minutes, about 105 minutes, about 120 minutes, about 150 minutes, or about 180 minutes. A sample of media can be taken after washing and/or the antibiotic treatment and analyzed to confirm removal or killing of bacteria not taken up be the host cells.

After incubation with the pathogen, the host cells are lysed. The host cells can be lysed using any agent or method known to be effective in lysing the host cells without also lysing or otherwise killing the pathogen. Lysing can be performed by chemical or mechanical means or a combination thereof. The lysing agent can be, but is not limited to, 0.05% Triton X-100. The host cells are incubated with the lysing agent for a period of time sufficient to lyse the host cells. The host cells can be incubated with the lysing agent for about 1 to about 30 minutes, about 1 minutes, about 2 minutes, about 3 minutes, about 4 minutes, about 5 minutes, about 6 minutes, about 7 minutes, about 8 minutes, about 9 minutes, about 10 minutes, about 12 minutes, about 14 minutes, about 16 minutes, about 18 minutes, about 20 minutes, about 22 minutes, about 24 minutes, about 26 minutes, about 28 minutes, or about 30 minutes. Certain host cells may require longer incubation times (i.e., >30 minutes).

Following lysis of the host cells, a sample of the lysate is collected and analyzed for the presence of pathogen. In some embodiments, the lysate sample is used to inoculate media suitable for growth of the pathogen and incubated under conditions suitable for growth of the pathogen. In some embodiments, the pathogen is incubated in an axenic culture. In some embodiments, the media contains an antibiotic or other compound that maintains selection of a nucleic acid that encodes the fluorescent protein.

In some embodiments, the amount of pathogen in the lysate is determined by measuring the level of the label in the sample. In some embodiments, amount of pathogen in the lysate in determined by measuring the level of fluorescence from the fluorescent protein in the sample. The amount of pathogen internalized by the host cells is proportional to the level of label detected in the lysate sample.

In some embodiments, measuring the amount of pathogen in the sample (lysate) comprises incubating the sample in media suitable for growth of bacteria, measuring the amount of label at regular intervals, and determining the time it takes to initially detect a label. In some embodiments, the fluorescence in the lysate sample is measured at regular intervals for 2-24 hours. In some embodiments, the fluorescence in the lysate sample is measured every 1, 2, 3, 4, 5, 6, 7, 8, 9, 10, 12, 14, 16, 18, or 20 minutes for 2-24 hours. Fluorescent signal is measured using appropriate excitation and emission wavelengths for the fluorescent label or protein using methods standard in the art. For example, the appropriate excitation and emission wavelengths appropriate to detect green fluorescent protein are 488 nm excitation wavelength and 520 nm emission wavelength. In some embodiments, the concentration of bacteria in the sample is also determined at regular intervals for 2-24 hours. The concentration of bacteria in the sample can be determined by measuring $OD_{600}$ of the sample signal every 1, 2, 3, 4, 5, 6, 7, 8, 9, 10, 12, 14, 16, 18, or 20 minutes for 2-24 hours. The time to detect initial fluorescence, the detection time (dT), is inversely proportional to the number of bacterial initially in the sample.

The methods can be used to quantify the level of uptake of the pathogen by the host cell and/or to quantify killing of the pathogen by the host cell. In some embodiments, the method further comprises comparing the level of uptake of the pathogen into the host cells treated with a compound of interest with uptake of the pathogen into host cells in a control sample that did not contain the compound of interest, wherein an increase in uptake of the pathogen in the sample with the compound relative to uptake of the pathogen in the control sample without the compound indicates the compound enhances uptake of the pathogen by the host cells. A decrease in uptake of the pathogen in the sample with the compound relative to uptake of the pathogen in the control sample without the compound indicates the compound suppresses uptake of the pathogen by the host cells. Compounds that modulate uptake of the pathogen by the host cells are then tested as host-targeting therapeutics for treating infection by the pathogen.

In some embodiments, the method further comprises comparing the level of pathogen recovered from host cells treated with a compound of interest after a certain amount of time with the level of pathogen recovered from host cells in a control sample that did not contain the compound of interest, wherein an increase in the level of the pathogen in the sample with the compound relative to level of the pathogen in the control sample without the compound indicates the compound suppresses killing of the pathogen by the host cells. A decrease in the level of the pathogen in the sample with the compound relative to level of the pathogen in the control sample without the compound indicates the compound enhances killing of the pathogen by the host cells. Compounds that modulate uptake of the pathogen by the host cells are then tested as host-targeting therapeutics for treating infection by the pathogen.

To quantify uptake, host cells are lysed immediately after infection. To quantify the ability of host cells (phagocytes) to kill intracellular bacteria, the host cells and bacteria are incubated for a prescribed amount of time after injection (interval) before lysing and assessing surviving bacteria The interval can be any interval from about 1 hour to about 72 hours. In some embodiments, surviving bacteria are assess after several intervals. In some embodiments, the intervals are 0 hours (to determine effect on uptake) and 1, 4, 6, and/or 24 hours (to determine effect on killing).

In some embodiments, the methods are performed in parallel to test a plurality of compounds for their individual effects on uptake of the pathogens by the host cells. In this way, a library of compounds can be tested to identify compounds that modulate uptake of the pathogens by the host cells.

In some embodiments, the methods further comprise analyzing the compounds that modulate uptake of the pathogen by the host cell for toxicity of the compound to the pathogen, the host cell, or and/or other host cells.

III. CFU-less Methods of Measuring Bacterial Growth Rate in Axenic Culture.

In some embodiments, methods for measuring bacterial growth rate in axenic culture are described. The methods comprise:

(a) expressing in the bacteria a fluorescent protein;

(b) growing the bacteria in axenic culture; and (c) measuring fluorescence in the culture at regular intervals.

In some embodiments, the methods can be used to determine the number of bacteria in a sample by determining earliest time point, $dT_{sample}$, at which the measured fluorescence value of the sample begins to increase; and comparing the $dT_{sample}$ with dT values obtained from a standard curve generated for a range of known CFUs of the bacteria in axenic culture.

The pathogen can be labeled using methods known in the art. In some embodiments, labeling the pathogen with a detectable marker comprises inserting an expressible gene encoding a fluorescent protein into the pathogen. In some embodiments, pathogenic bacteria are labeled by expressing a fluorescent protein in the bacteria. The fluorescent protein can be expressed from a plasmid or other expression vector present in the bacteria or the fluorescent protein can be expressed from a gene that is integrated into the genome of the bacteria. The bacteria can be transformed with nucleic acid, such as a plasmid, encoding the fluorescent protein or infected with a bacteriophage encoding the fluorescent protein. The fluorescent protein can be, but is not limited to, a green fluorescent protein, a blue fluorescent protein, a cyan fluorescent protein, a yellow fluorescent protein, an orange fluorescent protein, or a red fluorescent protein, or a derivative thereof.

The fluorescent protein can be, but is not limited to Green fluorescent protein (GFP), GFP-like proteins, modified GFPs, GFP derivatives, eGFP, eqFP611, Dronpa, TagRFPs, KFP, EosFP/IrisFP, Dendra, mVenus, mCherry, emerald GFP, superfolder GFP, Azami Green GFP, TagGFP, Turbo GFP, AcGFP, ZsGreen GFP, T-sapphire GFP, blue fluorescent protein, EBFP, EGFP2, Azurite BFP, mTagBFP, Cyan fluorescent protein (CFP), SCFP, mECFP, Cerulean CFP, mTurquoise CFP, CyPET CFP, AmCyanl CFP. Modori-Ishi Cyan CFP, TabCFP, mTFP (Teal), yellow fluorescent protein (YFP), Topax YFP, Venus YFP, mCitrine YFP, YPet YFP, TagYFP, PhiYFP, ZsYellow YFP, mBanana YFP, orange fluorescent protein (OFP), Kusabira Orange OFP, Kusabira Orange2 OFP, mOrange OFP, mOragne2 OFP, dTomato OFP, dTomato-Tandem OFP, TagRFP OFP, TagRFP-T OFP, DsRed OFP, DsRed2 OFP, DsRed-Express (T1) OFP, DsRed-Monomer OFP, mTangerine OFP, Red fluorescent protein (RFP), mRuby RFP, mApple RFP, mStrawberry RFP, AsRed2 RFP, mRFP1 RFP, JRed RFP, mCherry RFP, HcRedl RFP, mRaspberry RFP, dKeima-Tandem RFP, HcRed-Tandem RFP, mPlum RFP, and AQ143 RFP.

In some embodiments, the fluorescence in the sample is measured at regular intervals for 2-24 hours. In some embodiments, the fluorescence in the sample is measured every 1, 2, 3, 4, 5, 6, 7, 8, 9, 10, 12, 14, 16, 18, or 20 minutes for 2-24 hours. Fluorescent signal is measured using appropriate excitation and emission wavelengths for the fluorescent label or protein using methods standard in the art. For example, the appropriate excitation and emission wavelengths appropriate to detect green fluorescent protein are 488 nm excitation wavelength and 520 nm emission wavelength. In some embodiments, the concentration of bacteria in the sample is also determined at regular intervals for 2-24 hours. The concentration of bacteria in the sample can be determined by measuring $OD_{600}$ of the sample signal every 1, 2, 3, 4, 5, 6, 7, 8, 9, 10, 12, 14, 16, 18, or 20 minutes for 2-24 hours. The time to detect initial fluorescence, the detection time (dT), is inversely proportional to the number of initial bacterial in the sample.

IV. Modulation of Host Cell Function to Treat Infection.

The described methods can be used to search for and/or identify modulators of bacterial and/or viral uptake into host cells.

For some bacteria, such as extracellular bacteria, bacterial cell uptake, such as by macrophages, is a limiting step in clearing the bacterial infection. For these bacteria, the enhancement of uptake by host-targeting therapeutics can be used to increase the clearance of the infection. Compounds that enhance bacterial uptake can be used in host-targeting therapy against common extracellular pathogens, including, but not limited to, *Enterococcus* spp. (e.g., *Enterococcus faecium*), *Staphylococcus* spp. (e.g., *Staphylococcus aureus*), *Klebsiella* spp. (e.g., *Klebsiella pneumoniae*), *Acinetobacter* spp. (e.g., *Acinetobacter baumannii*), *Pseudomonas* spp. (e.g., *Pseudomonas aeruginosa*), and *Enterobacter* spp. Compounds can enhance uptake of bacteria by host cells as a standalone therapy or in combination with one or more known antibiotics to treat infection by bacteria. In some embodiments, compounds that enhance bacterial uptake by host cells may be selected from the compounds of Table 1.

For some bacteria, such as bacteria known for their intracellular growth and survival, compounds that inhibit bacterial uptake can be used as host-targeting therapeutics alone or in combination with known antibiotics to treat infection by bacteria. Such intracellular bacteria can be, but are not limited to, *Mycobacterium* spp., *Brucella* spp., *Rickettsia* spp., *Legionella* spp. (e.g., *Legionella pneumophila*), *Coxiella burnetii*, *Salmonella* spp., *Staphylococcus* spp., *Neisseria gonorrhoeae*, and *Listeria monocytogenes*. In some embodiments, compounds that inhibit bacterial uptake by host cells may be selected from the compounds of Table 2.

Host-targeting therapeutics, which target the host cell rather than the pathogen (e.g., bacteria or virus), can be used to treat antibiotic-resistant infection. Host-targeting compounds can modulate pathogen entry, enhance the ability of host cells to kill bacteria, and/or target host resources/nutrients and/or signaling pathways essential for intracellular survival and replication of the pathogen. Because host-targeting therapeutics target a host cell rather than a pathogen, they may circumvent antibiotic resistance.

Host-targeted therapeutics can also be effective across multiple pathogens, included, but not limited to: Tuberculosis (e.g., *Mycobacterium bovis*), Brucellosis (e.g., *Brucella abortus* and *Brucella ovis*), Pneumonia (e.g., *Legionella pneumophila*), Q-fever (e.g., *Coxiella burnetii*), Typhus (e.g., *Rickettsia conorii*), Hemorrhagic fever (e.g., Ebola virus), *K, pneumoniae, A. baumannii, P. aeruginosa*, and *E. coli*.

The described methods can be used to identify compounds useful in the prevention or treatment of disease or illness cause by bacterial infection. The disease or illness can be, but is not limited to tetanus, typhoid fever, diphtheria, syphilis, leprosy, Q fever, chlamydia, typhus, rickettsialpox, boutonneuse fever, African tick-bite fever, Rocky Mountain spotted fever, Flinders Island spotted fever, Queensland tick typhus, bartonellosis, tularemia, listeriosis, brucellosis, legionellosis, Legionnaires' disease, tuberculosis, nocardiosis, gonorrhea, bacterial meningitis, meningococcal septicemia, and plague.

In some embodiments, host-targeting compounds that modulate bacterial or viral uptake by host cells can be used in combination with one or more additional therapies. The additional therapies can be, but are not limited to, antibiotics, antibody therapies, immune modulators, antiviral drugs, anti-virulence therapies, and phage therapies.

In some embodiments, cell-based immunotherapies are described. Cell-based immunotherapies include, but are not limited to, obtaining or having obtained from a patient one or more blood stem cells, such as but not limited to monocytes; expanding or having expanded the stem cells; differentiating or having differentiated the stem cells to form macrophages; contacting or having contacted the macrophages with a host-targeted therapeutic known to modulated uptake of a pathogen by the macrophages to form activated macrophages, and infusing or having infused into the patient the activated macrophages. Uptake and/or killing of a pathogen by the macrophages can be measured using the methods described.

V. Kits

Also provided are kits comprising one or more reagents utilized in performing a method disclosed herein or kits comprising a composition, tool, or instrument disclosed herein.

For example, such kits can comprise a host cell and/or a labeled pathogen. Such kits can also comprise buffer, host cell growth media, pathogen growth media, host-cell impermeable antibiotic that is effective against the bacteria, host cell lysing agent, detergent, and suitable containers or receptacles. A kit may also include one or more control compounds known in modulate uptake of the pathogen by the host cell. In addition, a kit may further comprise instructional material which describes use of the kit to perform the methods disclosed herein. A kit may be used to identify compounds that modulate uptake of a pathogen by a host cell, measure growth of a pathogen in axenic culture, or determine the quantify of pathogen in a sample.

IV. Listing of Embodiments

1. A method for determining the effect of a compound on uptake of pathogens by host cells comprising:
    (a) labeling the pathogens with a detectable marker;
    (b) incubating a sample containing the host cells with the compound;
    (c) adding the labeled pathogens to the sample and incubating for a period of time sufficient for the labeled pathogen to enter the host cells;
    (d) lysing the host cells and collecting a lysate; and
    (e) determining a level of the pathogens internalized by the host cells by measuring the amount of label in the lysate.

2. A method for quantifying intracellular pathogens in host cells comprising:

(a) labeling the pathogens with a detectable marker;

(b) adding the labeled pathogens to a sample containing the host cells and incubating for a period of time sufficient for the labeled pathogens to enter the host cells;

(c) lysing the host cells and collecting a lysate; and (d) determining a level of the pathogens internalized by the host cells by measuring the amount of label in the lysate.

3. A method for identifying a host-targeting therapeutic comprising:

(a) labeling a pathogens with a detectable marker;

(b) incubating a sample containing host cells with a compound suspected of being a host-target therapeutic;

(c) adding the labeled pathogens to the sample and incubating for a period of time sufficient for the labeled pathogens to enter the host cells;

(d) lysing the host cells and collecting a lysate; and (e) determining a level of the pathogens internalized by the host cells by measuring the amount of label in the lysate.

4. The method of any one of embodiments 1-3, wherein determining a level of the pathogens internalized by the host cells comprises: using the lysate to inoculate a media suitable for growth of the pathogen, incubating the media under conditions suitable for growth of the pathogen, measuring the amount of label at regular intervals, and determining the time it takes to initially detect the label.

5. The method of any one of embodiments 1-4 wherein the method further comprises comparing the level of the pathogens internalized by the host cells with a level of pathogen internalized by the host cells in a control sample that did not contain the compound, wherein an increase in the level of pathogen internalized by the host cells in the sample relative to the level of pathogen internalized by the host cells in the control sample indicates the compound enhances uptake of the pathogen by the host cells, and a decrease in the level of pathogen internalized by the host cells in the sample relative to the level of pathogen internalized by the host cells in the control sample indicates the compound inhibits uptake of the pathogen by the host cells.

6. The method of any one of embodiments 1-5, further comprising determined the toxicity of the compound on the pathogen and/or the host cell.

7. The method of any one of embodiments 1-6, further comprising incubating the host cells with the compound for a period of time sufficient to allow the compound to bind to the host cells or to affect one or more cellular processes of the host cells after step (b).

8. The method of any one of embodiments 1-7, further comprising washing the host cells to remove compound(s) not associated with the host cells before adding the labeled pathogens.

9. The method of any one of embodiments 1-8, further comprising washing the host cells to remove pathogen that is not bound to or internalized by the host cells.

10. The method of any one of embodiments 1-9, wherein the host cell comprises a macrophage.

11. The method of any one of embodiments 1-9, wherein the macrophage comprises a primary macrophage and a cell culture cell.

12. The method of any one of embodiments 1-11, wherein macrophage comprises a monocyte-derived macrophage (MDM), bone marrow-derived macrophage (BMDM), THP1 cell, or a RAW264.7 cell.

13. The method of any one of embodiments 1-12, wherein labeling the pathogen with a detectable label comprises expressing a fluorescent protein in the pathogen.

14. The method of any one of embodiments 1-13, wherein the pathogen is a bacterium.

15. The method of embodiment 14, wherein the pathogen is a gram-positive bacterium or a gram-negative bacterium.

16. The method of any one of embodiments 1-12, wherein the pathogen is a virus.

17. A method of treating a bacterial infection in a patient comprising administering to the subject an enhancer or suppressor of bacterial uptake.

18. The method of embodiment 17, wherein the enhancer is selected from the group consisting of: thiamylal, amlexanox, cefaclor, floxuridine, miltefosine, mitoxantrone, loperamide, doramectin, aminacrine, mebeverine, aminohippuric acid, fipexide, heptaminol, nicergoline, and menthyl benzoate.

19. The method of embodiment 18, wherein the suppressor is selected from the group consisting of: cefotetan, colistimethate, colistin, gentian violet, polymyxin B, berbamine, 7,2'-dimethoxyflavone, dehydroabietamide, fluticasone, gambogic acid, chlorquinaldol, anthothecol, quinacrine, cepharanthine, mitomycin, sanguinarium, triflupromazine, cysteamine, tenatoprazole, tilorone, methionine sulfoximine, cypermethrin, and temazepam.

20. A method of inhibiting uptake of bacteria by a macrophage comprising contacting the macrophage with quinacrine.

21. A method of treating a pathogenic infection in a subject comprising administering to the subject one or more compounds that (a) modulate uptake of the pathogen by one or more cells of the subject; (b) enhance the ability of one or more cells of the subject to kill the pathogen, and/or; (c) target one or more host resources and/or signaling pathways essential for intracellular survival and/or replication of the pathogen.

22. The method of embodiment 21, wherein the compound causes an increase or decrease in the level of pathogen in a host cell as measured in a CFU-less assay.

23. A method of determining bacterial survival in a host cell comprising (a) labeling the bacteria with a detectable marker;

(b) adding the labeled bacteria to the sample containing the host cells and incubating for a period of time sufficient for the labeled pathogens to enter the host cell;

(c) lysing the host cells and collecting a lysate; and (d) determining the amount of pathogen in the host cells by measuring the amount of label in the lysate.

24. A method for measuring growth of bacteria in axenic culture comprising:

(a) expressing a fluorescent protein in the bacteria;

(b) growing the bacteria in axenic culture;

(c) measuring fluorescence in the culture at regular intervals.

25. A kit for performing a CFU-less assay comprising: host cells, bacteria expressing a fluorescent protein and/or an expression vector for expressing a fluorescent protein in bacteria, and instructions for use; and optionally one or more of: host cell growth media, bacteria growth media, wash buffer, multi-well plate, a host-cell impermeable antibiotic that is effective against the bacteria, and a host cell lysing agent.

EXAMPLES

Example 1.

Identification of Compounds That Enhance or
Inhibit Bacterial Uptake

A library of 2,400 approved drugs was assayed to search
for modulators of Escherichia coli uptake by RAW 264.7
macrophages. Thirty-eight compounds were identified. Of
the thirty-eight bacterial uptake modulators identified, fif-
teen enhanced uptake by one standard deviation from con-
trol (Table 1) and twenty-three inhibited bacterial uptake by
three standard deviations from control (Table 2) at concen-
trations that did not exhibit cytotoxicity to the host cells.
These compounds could also act on bacteria by accumula-
tion in the host cells. One of the uptake inhibitors, quina-
crine, attenuated infection by *Salmonella, Pseudomonas,
Klebsiella*, and *Acinetobacter* species, demonstrating the
efficacy of the methods in identifying host-targeting com-
pounds that can be used in the treatment of broad antibiotic-
resistant infections.

Figure 1:
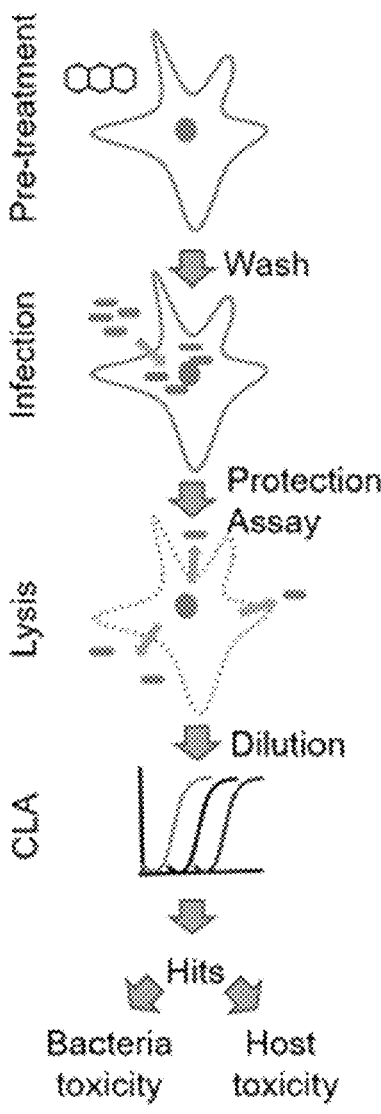
FIG. 1. Illustration of CFU-less assay (CLA) for measuring an effect of a compound of interest on uptake of bacterial by a host cell with optional toxicity analyses.
Figure 2:
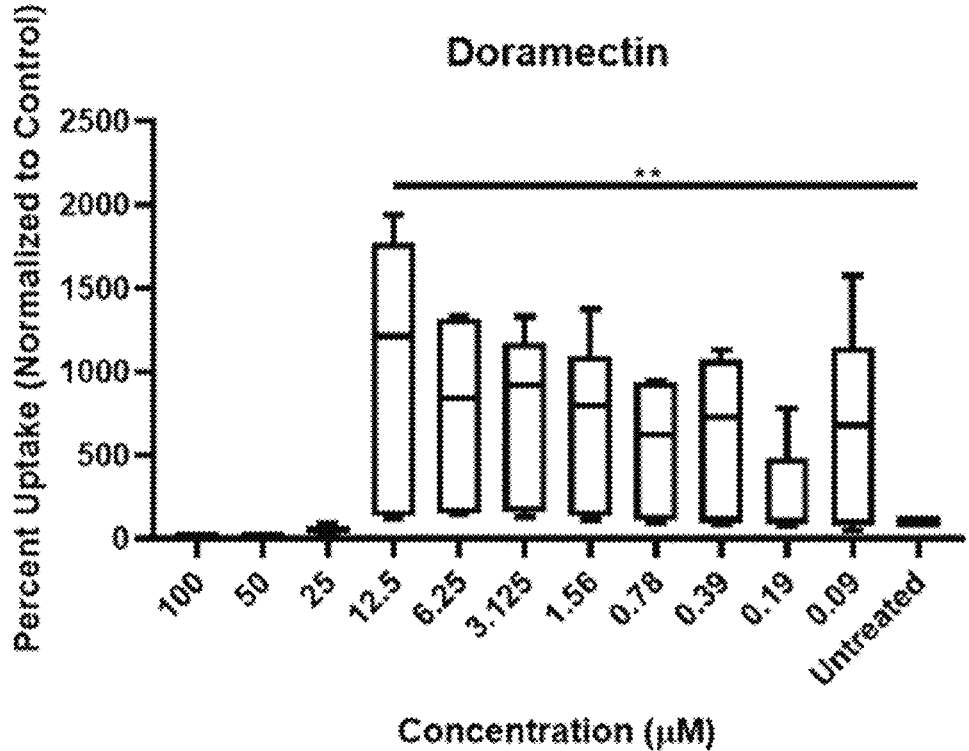
FIG. 2. Graph illustrating an increase in bacterial uptake in the presence of doramectin.

The effect of Doramectin on uptake is shown in FIG. 2.
CFU plating was performed to confirm the enhancement.

TABLE 1

| Enhancers of Uptake (1 Standard deviation) | |
|---|---|
| Compound Name | Bioactivity |
| Thiamylal sodium | Anesthetic |
| Amlexanox | Anti-allergic |
| Cefaclor | Antibacterial |
| Floxuridine | Antineoplastic |
| Miltefosine | Antineoplastic |
| Mitoxantrone hydrochloride | Antineoplastic |
| Loperamide hydrochloride | Calcium channel blocker |
| Doramectin | Endoparasitic |
| Aminacrine | Local antiseptic |
| Mebeverine hydrochloride | Muscle relaxant |
| Aminohippuric acid | Renal function diagnosis |
| Fipexide hydrochloride | Psychostimulant |
| Heptaminol hydrochloride | Vasodilator |
| Nicergoline | Vasodilator |
| Menthyl benzoate | Synthesis of benzaldehyde |

TABLE 2

| Inhibitors of Uptake (3 Standard deviations) | |
|---|---|
| Compound Name | Bioactivity |
| Cefotetan | Antibacterial |
| Colistimethate sodium | Antibacterial |
| Colistin sulfate | Antibacterial |
| Gentian violet | Antibacterial |
| Polymyxin B sulfate | Antibacterial |
| Berbamine hydrochloride | Antihypertensive |
| 7,2'-Dimethoxyflavone | Anti-inflammatory |
| Dehydroabietamide | Anti-inflammatory |
| Fluticasone propionate | Anti-inflammatory |
| Gambogic acid | Anti-inflammatory |
| Chlorquinaldol | Anti-infectant/Antifungal |
| Anthothecol | Antimalarial |
| Quinacrine hydrochloride | Antimalarial/Anthelmintic |
| Cepharanthine | Antineoplastic |
| Mitomycin | Antineoplastic |
| Sanguinarium chloride | Antineoplastic |
| Triflupromazine hydrochloride | Antipsychotic |
| Cysteamine hydrochloride | Antiurolithic |
| Tenatoprazole | Anti-ulcer/Proton pump Inhibitor |
| Tilorone | Antiviral |

TABLE 2-continued

| Inhibitors of Uptake (3 Standard deviations) | |
|---|---|
| Compound Name | Bioactivity |
| Methionine sulfoximine | Glutamine synthetase inhibitor |
| Cypermethrin | Insecticide |
| Temazepam | Sedative |

Example 2

Macrophage Killing of Pathogenic Bacteria

Figure 3:
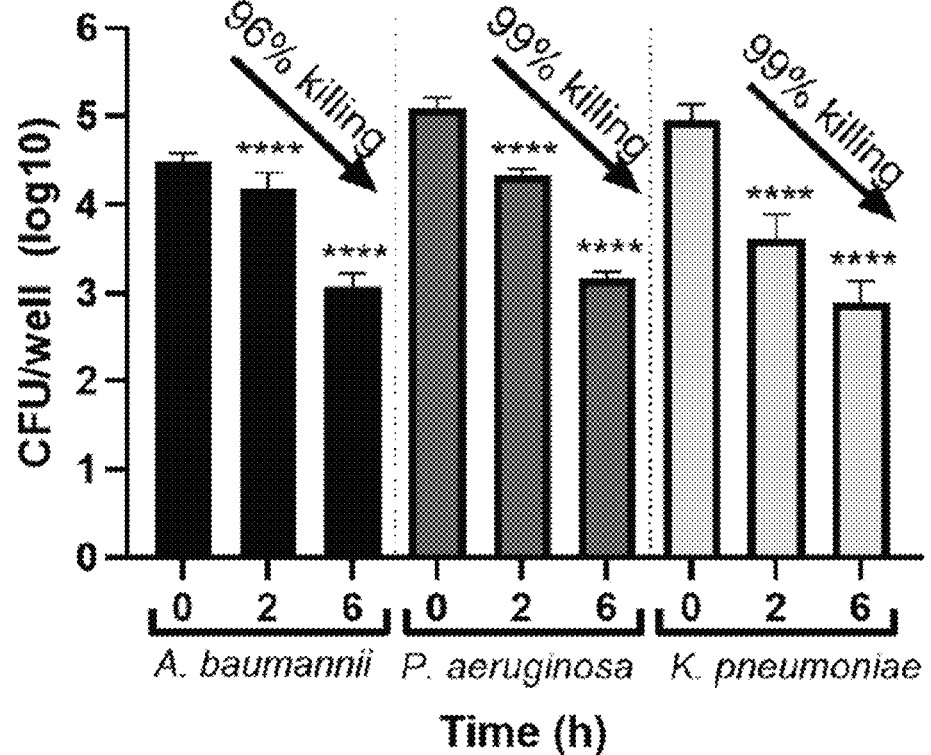
FIG. 3. Graph illustrating rate of killing of bacteria by macrophages.
Figure 4:
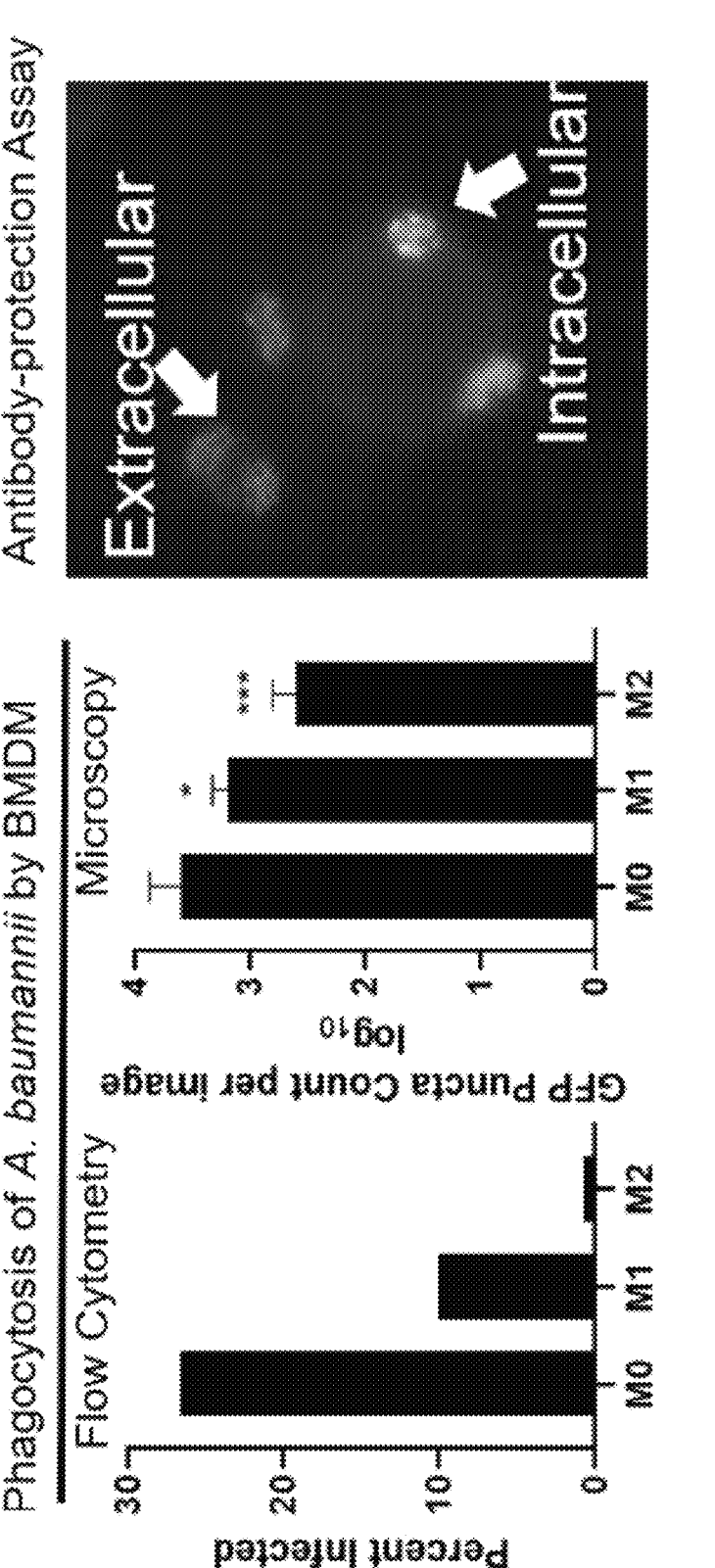
FIG. 4. Graph illustrating phagocytoses of *A. baumannii* by bone marrow derived macrophages (left panel) and micrograph showing antibody detection of external and internal bacteria (right panel).
Figure 5:
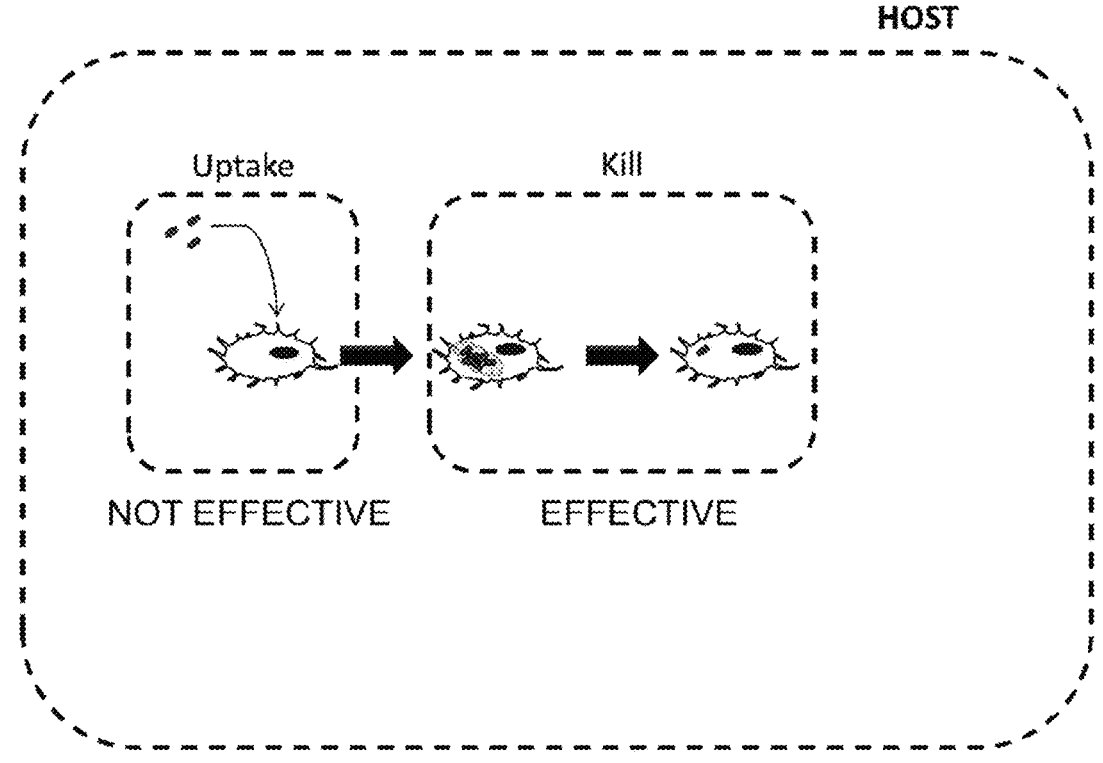
FIG. 5. Illustration of enhancement of killing of bacteria by enhancement of phagocytosis by macrophages.

For some pathogens, uptake is the rate-limiting step in
clearing the pathogen. Macrophages can effectively kill the
pathogen, but uptake of the pathogen by the macrophage is
not efficient (FIG. 3-5).

Example 3

CFU-less Assay (CLA) to Assess Bacterial Uptake

Figure 6:
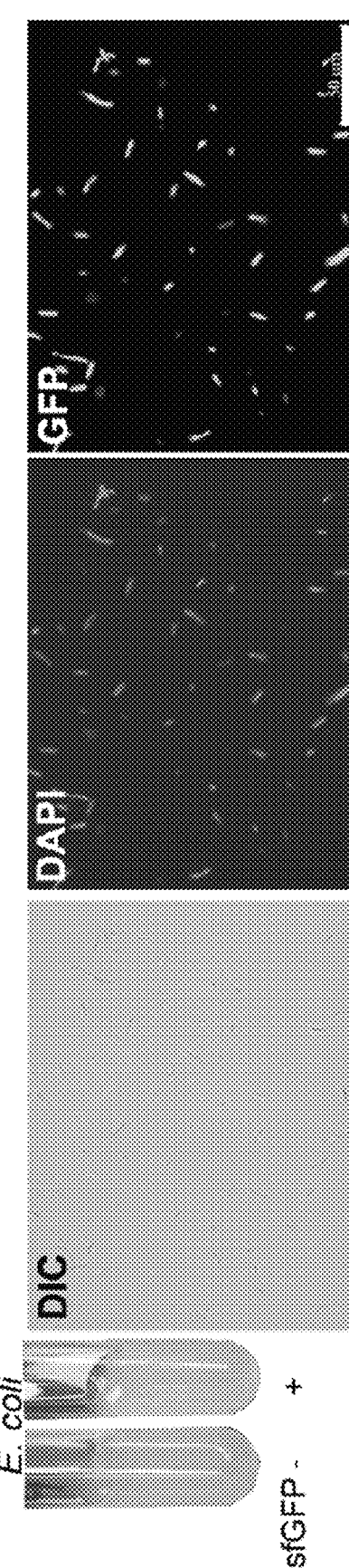
FIG. 6. Image showing liquid culture of *E. coli* strain DH5α, expressing control vector (−) or sfGFP (+) (far left image) and micrographs showing *E. coli* strain DH5α, expressing or sfGFP, DIC image, DAPI image showing nucleic acid staining and fluorescence image showing sfGFP fluorescence. Scale bar is 50 μm FIG. 7. Illustration of CFU-less assay (CLA) for measuring an effect of a compound of interest on uptake of bacteria or virus by a host cell using fluorescent protein-expressing bacteria.
Figure 7:
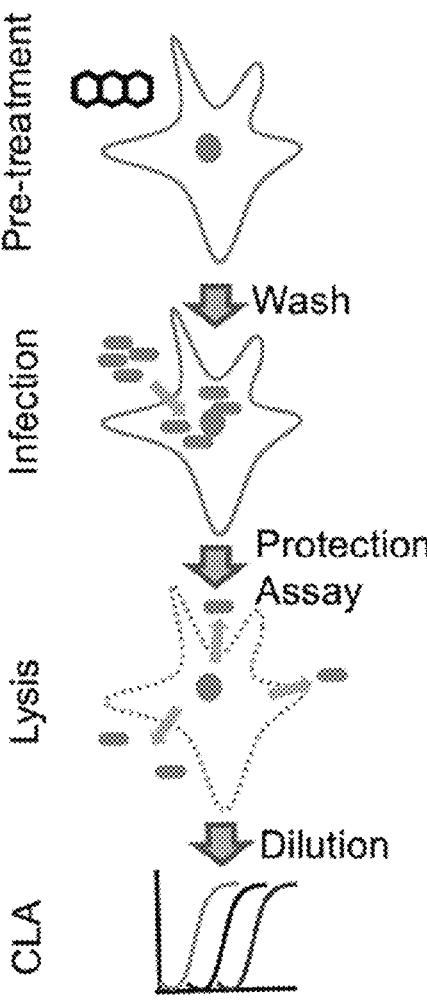
Figure 8:
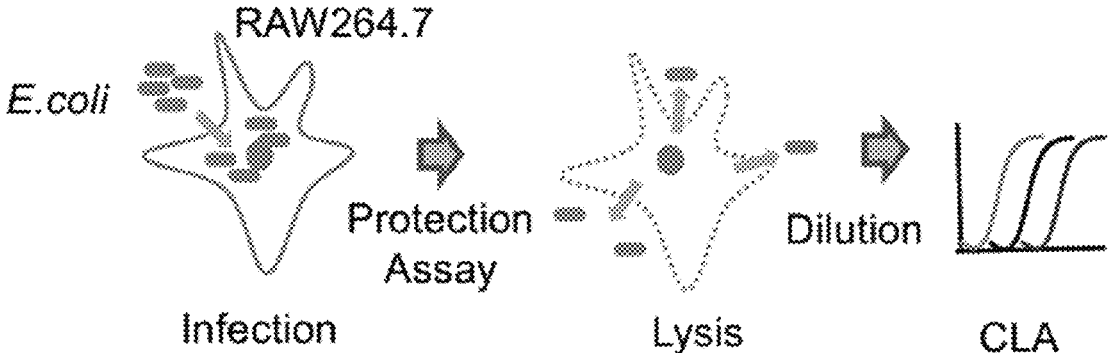
FIG. 8. Illustration of the CFU-less assay (CLA) quantitating bacteria internalized by a host cell and/or bacteria that remain viable after internalization by a host cell FIG. 9. Graphs illustrating sensitivity of detection of bacteria using the CFU-less assay (left panel) and the inverse relationship between dT determined by the CFU-less assay and CFUs (right panel).

Described are methods of quantifying the level of uptake
of a pathogen by a host cell that does not require determining
colony-forming units. The pathogen is first labeled with a
detectable marker. In some embodiments, a bacterial patho-
gen is transformed with a plasmid expressing a fluorescent
protein, such as superfolder green fluorescent protein
(sfGFP). In some embodiments, the pathogen, such as *E.
coli* DH5α, is transformed with a plasmid, pON-sfGFP
(FIG. 6-8). Expression of sfGFP in *E. coli* and fluorescence
detection is shown in FIG. 6. FIG. 7 illustrates, broadly, a
method for determining the rate of uptake of labeled bacteria
by host cells. FIG. 8 illustrates determination of *E. coli*
uptake by RAW264.7 macrophages using CFU-less detec-
tion.

Figure 9:
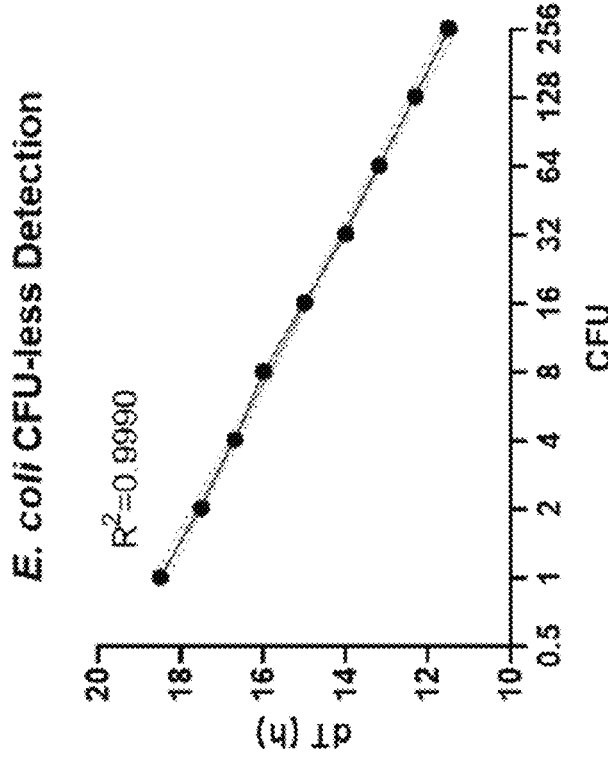
Figure 9:
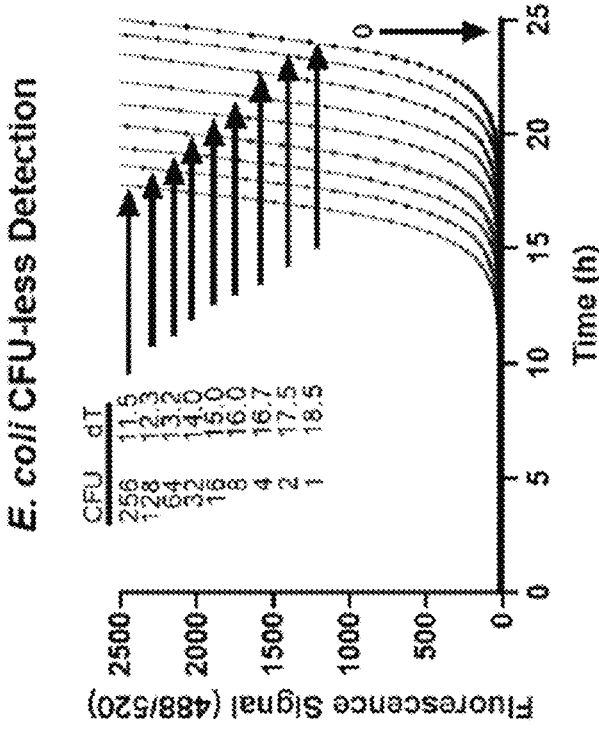
Figure 10:
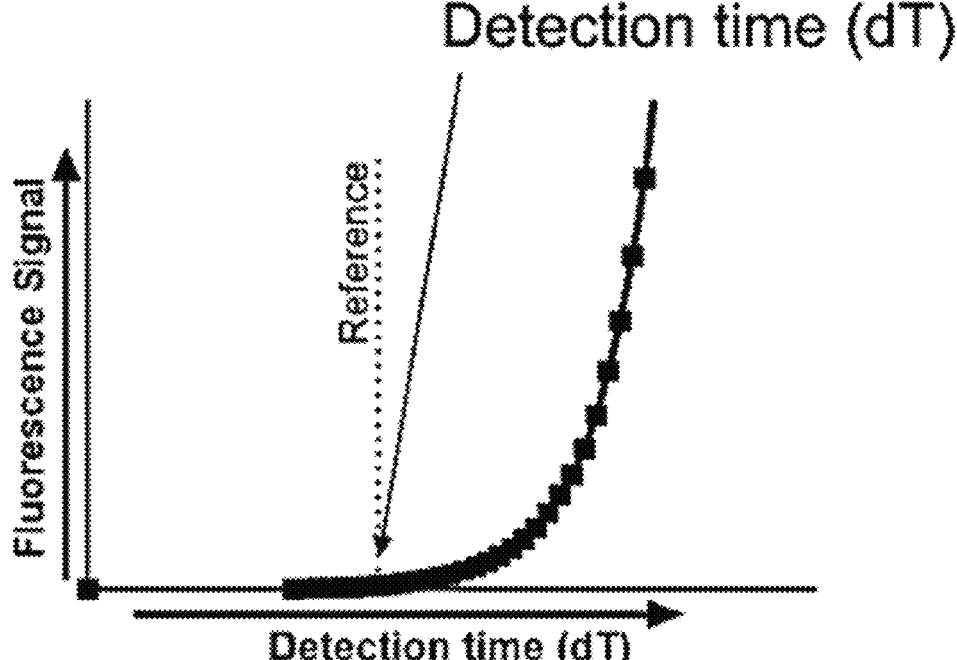
FIG. 10. Graphs illustrating a representation of determination of detection time (dT) in a CFU-less assay.
Figure 11:
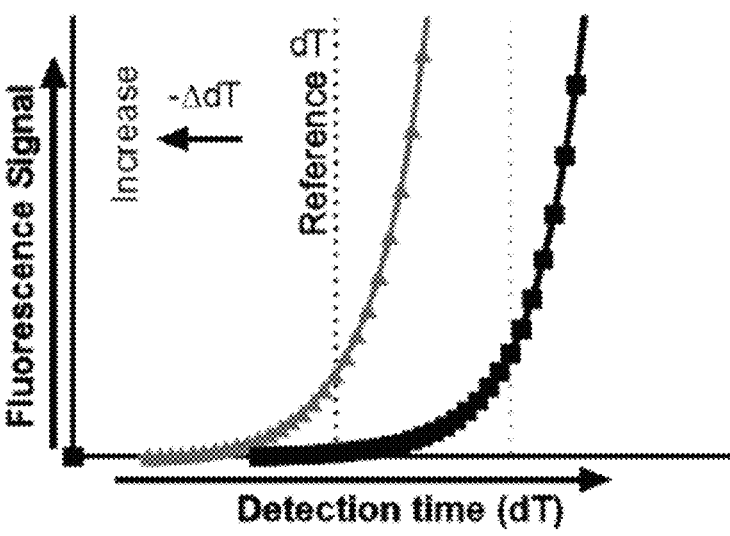
FIG. 11. Graph illustrating a representation of fluorescence measured in the CFU-less assay and the shift in detection for increase in internalization of bacteria by the host cell relative to a reference sample.
Figure 12:
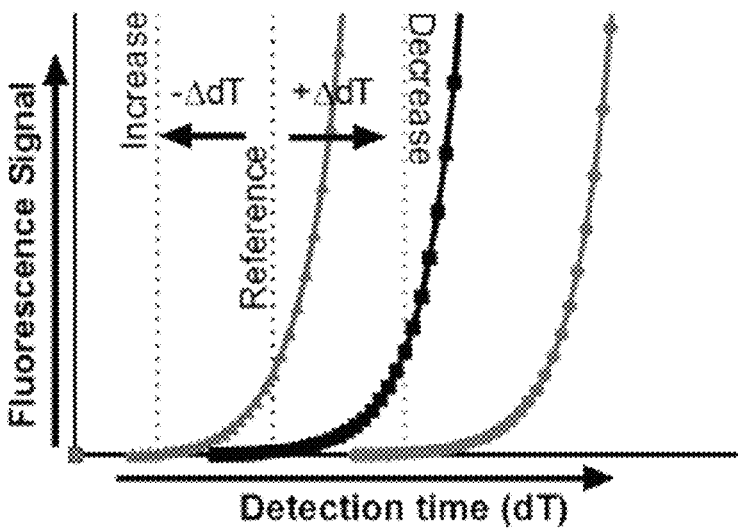
FIG. 12. Graph illustrating a representation of fluorescence measured in the CFU-less assay and the shift in detection for increase or decrease in internalization of bacteria by a host cell relative to a reference sample.
Figure 13:
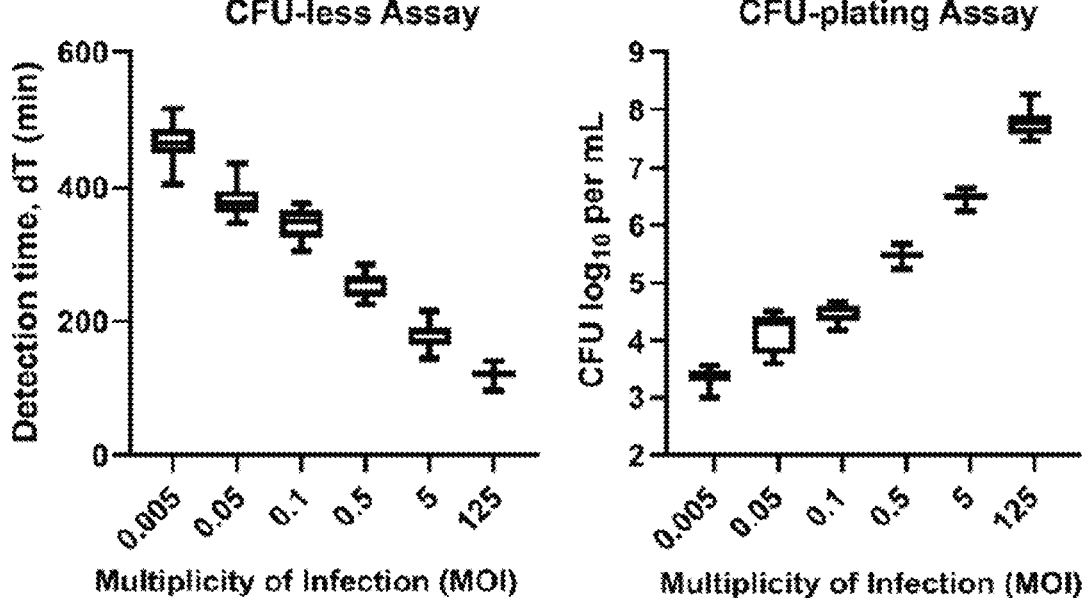
FIG. 13. Graphs illustrating correlation of quantitation of intracellular bacteria using the CFU-less assay (left panel) with CFU determination (right panel).
Figure 14:
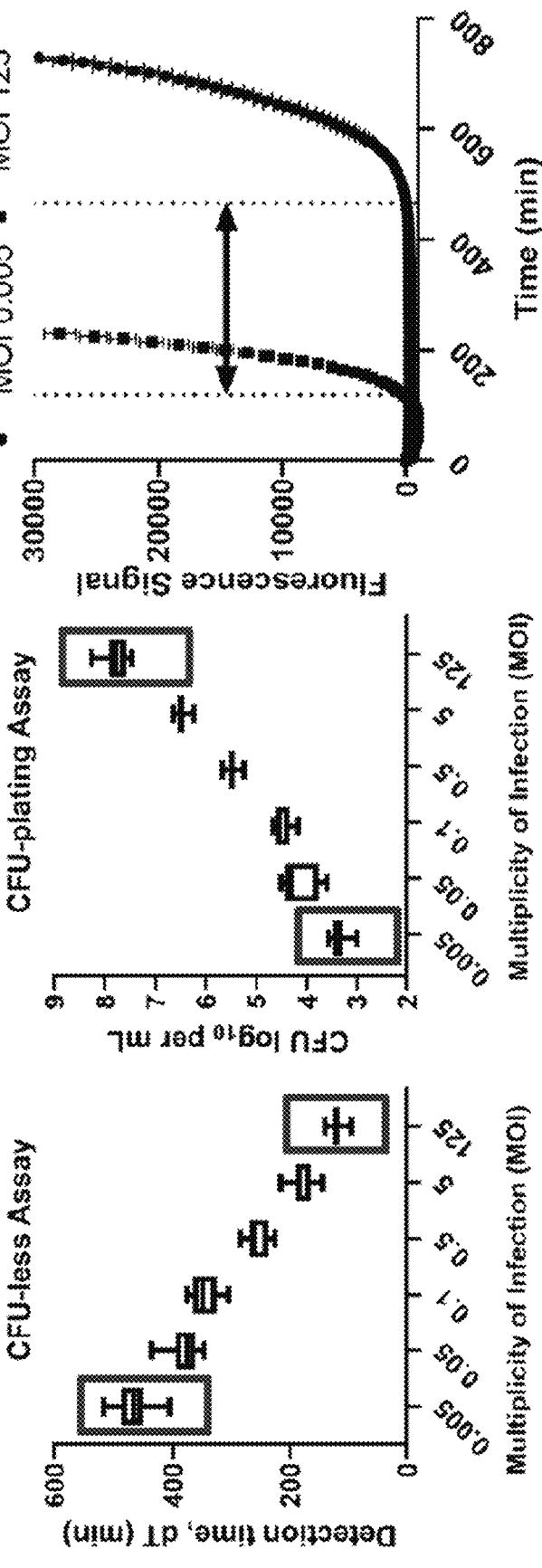
FIG. 14. Graphs illustrating correlation of dT (left panel) and CFU (middle panel) with MOI and growth curves generated using fluorescence signal at 0.005 and 125 MOI (right panel).
Figure 15:
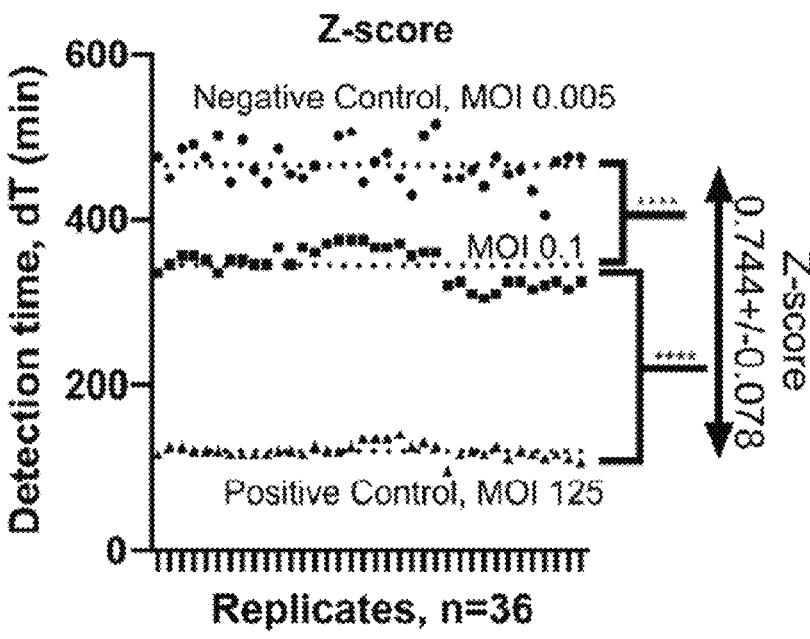
FIG. 15. Graph illustrating reproducibility of the CFU-less detection assay.
Figure 16:
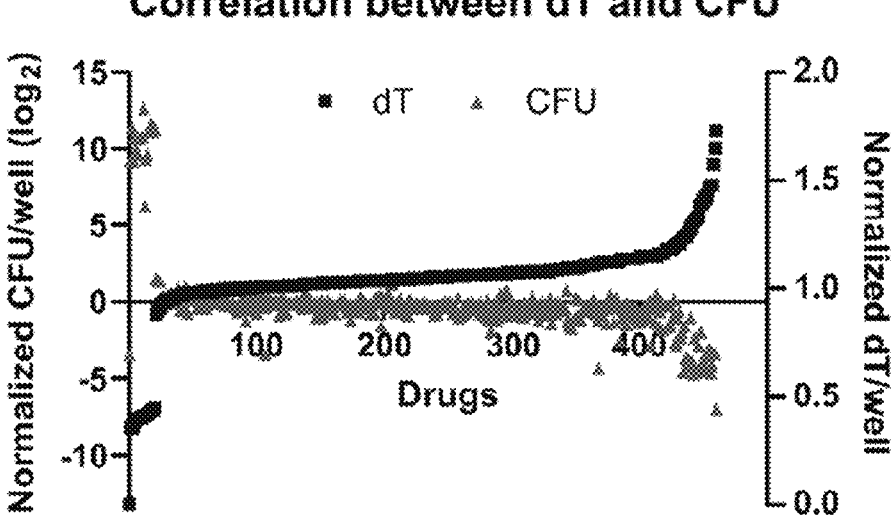
FIG. 16. Graph illustrating quantitation of bacteria in the presence a number of drugs using the CFU-less assay (squares) and CFU determination (triangles).

As shown in the FIGS. 9-12, the CFU-less assay (CLA)
is very sensitive, able to detect minor changes in colony
forming units (CFUs). As shown in FIG. 9, the CFU-less
assay was able to detect *E. coli* at a CFU of 1. Further, the
CFU-less assay was able to quantitatively detect the amount
of *E. coli* in the sample. Also as shown in FIG. 9, dT as
determined by the CFU-less assay was inversely propor-
tional to CFUs. FIG. 10 graphically illustrates determination
of detection time. FIG. 11 graphically illustrates detection of
a shift in detection time correlating with an increase in host
cell uptake of the labeled bacteria. FIG. 12 graphically
illustrates detection of shifts in detection time correlating
with an increase and decrease in host cell uptake of the
labeled bacteria.

Comparison of data from CLU-less assay and CFU-
plating assay (FIG. 13-16). As shown in FIGS. 13-16, the
CFU-less assay can be used to quantitatively measure the
amount of labeled bacteria in a sample. Comparison of data
from the CLF-less assay and CFU-plating assay demon-
strated the accuracy and reproducibility of the CFU-less
assay.

Example 4

Screen Optimization

Figure 17C:
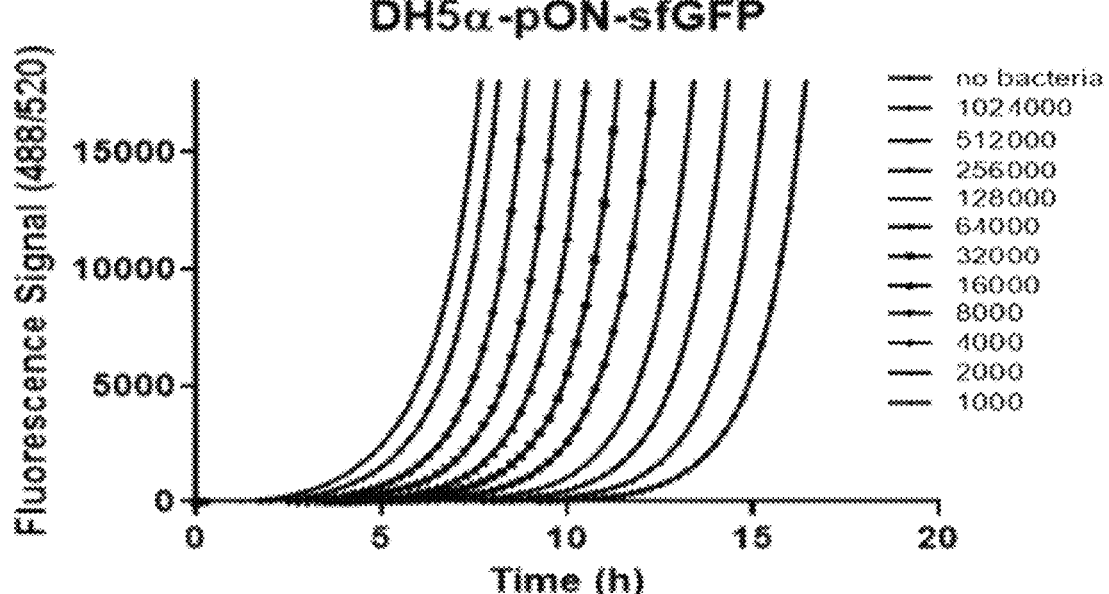
FIG. 17C. Graph illustrating titration of CFUs and detection of *E. coli* in the CFU-less assay. Detection time increases with increasing CFU dilutions.

Titrations of multiplicity of infections (MOIs) were per-
formed to find the controls for the screen using the Z' factor
as the determining factor between the positive and negative
controls (FIG. 17). Observed Z' factors between 0.4-1.0 indicated the CFU-less assay is suitable for use in high throughput screens. Good separation was observed between the positive and negative controls and a midpoint to use to determine enhancement or inhibition of uptake of bacteria.

Example 5

Screen of 2,400 Approved Drugs for Modulators of Bacterial Uptake

Figure 18:
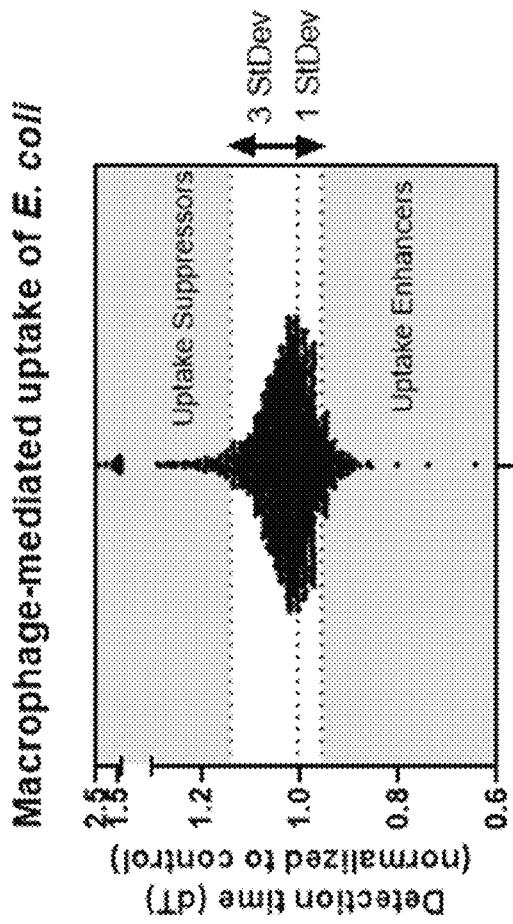
FIG. 18. Illustration of assay to search for drugs that modulate uptake of bacteria into macrophages (left panel)
Figure 18:
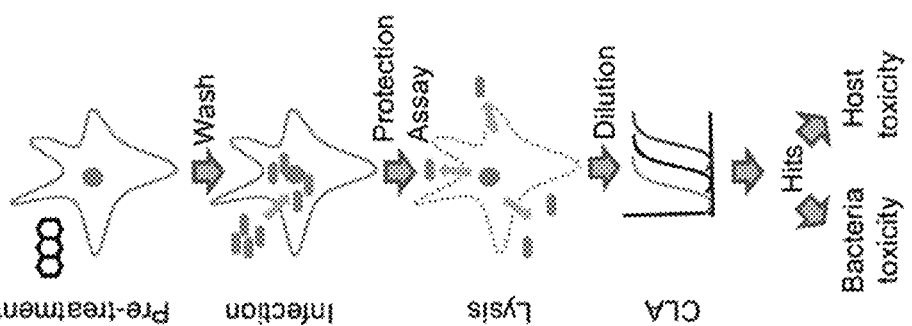

A screen of 2400 existing approved drugs was performed using the described assay to identify compounds that modulate macrophage uptake of *E. coli*. The results are summarized in the Tables 1 and 2 and FIG. 18. The results demonstrate the enhancement or inhibition of uptake by each of the 2,400 compounds and the MOI controls. The hits were 3 standard deviations away from the mean of the MOI 0.1 control. Only 16 compounds were cytotoxic (see example 6 below). As indicated in example 1, the screen of 2,400 approved drugs yielded Thirty-eight modulators of bacterial uptake (FIG. 18, Table 1, Table 2).

2,400 compounds were screened and compounds that target the host to enhance or inhibit uptake of bacteria were identified. This screen confirms the utility of the CFU-less assay. Quinacrine was identified as a compound that decreases the intracellular load of bacteria. These compounds could be used as a therapeutic for intracellular bacterial infections.

Example 6

CFU-less Assay to Assess Bacterial Uptake

Provided below is an exemplary protocol for a CFU-less assay to assess bacterial uptake
1. Seed a tissue culture treated plate at desired cell concentration of host cells a. e.g., in 96-well plate, 100,000 host cells/well and 100 µL volume/well
2. prepare a culture of desired pathogen, e.g., bacteria
3. Allow the host cell culture and the pathogen culture to incubate overnight at 37° C. and 5% $CO_2$ and 37° C., respectively
4. Add a compound of interest to the host cells and incubate at 37° C. in 5% $CO_2$ for 1 to 24 hours
5. Remove media from host cell culture wells
6. Wash host cells two times with phosphate-buffered saline (PBS) and add 100 µL media per well
7. Infect host cells with desired multiplicity of infection of pathogen
8. Parafilm plate
9. Centrifuge plate for 30 minutes at 2200 rpm and 37° C.
10. Carefully remove parafilm
11. Incubate plate for 30 minutes at 37° C. and 5% $CO_2$
12. Remove media from cells
13. Add 100 µL of culture media+100 µg/mL gentamicin
14. Incubate plate for 1 hour at 37° C. and 5% $CO_2$
15. Plate 10 µL of supernatant on Luria broth (LB) agar plates to check that gentamicin has killed all extracellular pathogen
16. Remove remaining media from cells
17. Wash two times with PBS
18. Add 100 µL of 0.05% Triton X-100
19. Incubate plate for 18 minutes at 37° C. and 5% $CO_2$
20. After incubation, pipet up and down 12 times to lyse cells and mix lysate 21. Transfer 10 µL of lysate into black clear-bottom 96-well plate that has 190 µL of LB (+antibiotics if needed)
22. Read plate for 24 hours, every 5 minutes, at 37° C., shaking for 5 seconds, $OD_{600}$, $OD_{488/520}$ (for GFP)

To calculate dT
23. The fluorescence value determined at the first time point (e.g., t=0) is subtracted from the fluorescence value measurement at each successive time point
24. The first time point at which the fluorescent values begin to increase without a subsequence decrease is dT. (As an example: for fluorescent values 0, 6, 6, 7, 8, 6, 8, 9, 10, 11, 14, . . . the fluorescence value of 9 represents an increase in fluorescence without a subsequence decrease and the time point for measurement of the fluorescence value of 9 is dT)

Provided below is another exemplary protocol for a CFU-less assay to assess bacterial uptake
1. Seed host cells in a multi-well tissue culture and incubate at 37° C. in 5% $CO_2$ (or other appropriate conditions for the host cells)
2. Incubate bacteria expressing a fluorescent protein in culture at an appropriate temperate, e.g., 37° C.
3. Treat the host cells with a compound of interest. Add a compound of interest to the host cells and incubate at 37° C. in 5% $CO_2$ for 1, 2, 3, 4, 5, 6, 7, 8,9, 10, 11, 12, 13, 14, 15, 16, 17, 18, 19, 20, 21, 22, 23, or 24 hours. In some embodiments, the compound of interest is incubated with the host cells for 4 hours
4. Wash host cells with isotonic buffer or, e.g., PBS, or growth media 1, 2, 3, 4, or 5 times and add growth media to the cells
5. Add bacteria to host cell at a multiplicity of infection (MOI) of 0.005-125, 0.005, 0.05, 0.1, 0.2, 0.3, 0.4, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, or 125. In some embodiments, the MOI is 0.1
7. Incubate host cells with the bacteria for 15-180, 15, 20, 25, 30, 35, 40, 45, 60, 75, 90, 120, 150, or 180 minutes at 37° C. in 5% $CO_2$ (or other appropriate conditions for the host cells)
8. Remove media from cells and optionally wash cells
9. Add growth media and an antibiotic that does not enter the host cells to kill bacteria not taken up by the host cells
10. Incubate plate for 30-180, 30, 45, 60, 75, 90, 120, 150, or 180 minutes at 37° C. and 5% $CO_2$ (or other appropriate conditions for the host cells)
11. Optionally collect a sample of the media and plate on bacteria growth media to confirm the antibiotic killed all extracellular bacteria
12. Remove remaining growth media from cells
13. Wash cells 1-5, 1, 2, 3, 4, or 5 times with isotonic buffer, e.g., PBS
14. Add cell lysing agent, such as, but not limited to, 0.05% Triton X-100
15. Incubate cells for 1-30, 1, 2, 3, 4, 5, 6, 7, 8, 9, 10, 12, 14, 16, 18, 20, 22, 24, 26, 28, or 30 minutes at 37° C. and 5% $CO_2$ (or other appropriate conditions for the host cells)
16. Agitate or mix cell and buffer to lyse host cells and mix lysate
17. Transfer a sample (inoculant) of the lysate to bacteria growth media in a multi-well plate, such as a black clear-bottom 96-well plate and incubate at 37° C. The bacteria growth media may contain an antibiotic or other compound that maintains selection of a nucleic acid (e.g., plasmid) in the bacteria that contains the gene for the fluorescent protein 18. Read plate by measuring $OD_{600}$ to determine bacteria concentration and measure fluorescent signal every 1, 2, 3, 4, 5, 6, 7, 8, 9, 10, 12, 14, 16, 18, or 20 minutes for 2-24 hours, at e.g., 37° C., shaking for 5 seconds before each reading. Fluorescent signal is measured using appropriate excitation and emission wavelengths for the fluorescent label or protein using methods standard in the art. For example, the appropriate excitation and emission wavelengths appropriate to detect green fluorescent protein are 488 nm excitation wavelength and 520 nm emission wavelength To calculate dT 19. Subtract the fluorescence value determined at the first time point from the fluorescence value determined at each successive time point 20. Determine the time point, dT, at which the determined fluorescence value is higher than the fluorescence value determined for the immediate prior time point, with a subsequent decrease in fluorescence value (i.e., the time point at which the fluorescence values begin to increase without fluctuation). For example, if there is a fluctuation then the next value that is higher than the fluctuating number is used.

21. The time it takes to detect initial fluorescence, the detection time (dT), is inversely proportional to the number of initial bacterial in the sample (from step 17).

Determine whether a compound of interest increases or decreases the rate of internalization by the host cell.

22. An increase in dT relative to dT determined for a control sample (e.g., absence of treatment) indicates the compound decrease the rate of internalization of the bacteria. A decrease in dT relative to dT determined for a control sample (e.g., absence of treatment) indicates the compound increases the rate of internalization of the bacteria.

Provided below is another exemplary protocol for a CFU-less assay to assess bacterial uptake 1. Seed host cells in a multi-well tissue culture and incubate at conditions suitable for growth of the host cells.

2. Add bacteria expressing a fluorescent protein to the host cells either concurrently with or subsequent to incubation of the host cells with one or more compounds of interest. In some embodiments, the host cells are incubated with the compound of interest for 1-24 hours prior to adding the bacteria. In some embodiments, the bacteria are added to the host cells and a multiplicity of infection (MOI) of 0.005-125. The cells can be washed to remove the extracellular compound of interest prior to adding the bacteria.

3. Incubate host cells with the bacteria for sufficient time to allow internalization of the bacteria by the host cells, e.g., 15-240 minutes. In some embodiments, after incubation of the host cells with the bacteria, the cells are washed and/or treated with an antibiotic that does not enter the host cells and kills bacteria not taken up by the host cells. In some embodiments, the cells are incubated 15-240 minutes with the antibiotic. In some embodiments the cells are washed following incubation with the antibiotic.

4. Lyse the host cells.

5. Transfer a sample of the lysate to media suitable for growth of the bacteria and incubate in conditions suitable for growth of the bacteria.

6. Measure fluorescence (using conditions suitable for detection of the fluorescent protein expressed in the bacteria) and optionally $OD_{600}$ at regular intervals (time points) for 1-25 hours.

7. Determine dT based on the earliest time point at which the measured fluorescence value of the sample begins to increase, wherein dT is proportional to the amount of bacteria internalized by the host cells. In some embodiments, dT is compared with dT for a control sample (e.g., in the absence treatment of host cells with a compound of interest). An increase in dT relative to dT determined for the control sample indicates the compound decreases the rate of internalization of the bacteria relative to the control. A decrease in dT relative to dT determined for a control sample indicates the compound increases the rate of internalization of the bacteria relative to the control.

In some embodiments, dT is compared with a standard curve to quantitate the number of bacteria initially present in the sample. The standard curve can be generated by determining dTs for a range of MOIs of the bacteria in axenic culture.

Example 7

Axenic Growth

The CFU-less assay can reliably detect compound cytotoxicity in axenic medium. The compound(s) of interest were combined with either the host cell or the pathogen in an axenic medium to analyze toxicity of the compound(s) on the host cell or pathogen. The graphs below show an example of how the compounds from the screen affect axenic growth of *E. coli*. The effects of the compounds on axenic growth of *E. coli* were minimal. The majority of the compounds tested demonstrate normal growth curves (FIGS. 19-20).

Example 8

Quinacrine Cytotoxicity to Bcteria in Axenic Culture

Quinacrine HCl had an inhibitory effect on intracellular survival of both intracellular and extracellular bacterial strains in RAW 264.7 macrophages. This confirms the results of the screen and expands potential uses. Quinacrine was previously known as an antiparasitic, an anti-inflammatory agent, intrapleural sclerosing agent, a pneumothorax prophylaxis, Creutzfeldt-Jakob disease (CJI)) therapy, and as an anticancer agent (FIG. 21).

Example 9

Inhibiting Bacteria Uptake Using a Host-Targeting Therapeutic in Combination With Additional Therapeutics A host-targeting therapeutic can be combined with a known antibiotic to improve the treatment of infection. Exemplary, infections include, but are not limited to, Tuberculosis (e.g., *Mycobacterium tuberculosis, Mycobacterium bovis*), Brucellosis (e.g., *Brucella abortus, Brucella ovis*), Pneumonia (e.g., *Legionella pneumophila*), Q-fever (e.g., *Coxiella burnetii*), Typhus (e.g., *Rickettsia conorii*), Salmonellosis (e.g., *S. enterica*), Gonorrhea (e.g., *N. gonorrhoeae*), and Listeria (e.g., *L. monocytogenes*).

In some embodiments, the host-targeted therapeutic inhibits uptake of the pathogen by the host cell (FIG. 22).

In some embodiments, the host-targeted therapeutic enhances uptake of the pathogen by the host cell. The host cell can be, but is not limited to, a macrophage. Enhancing bacterial uptake by phagocytic macrophages can be used systemically or in a cell-based immunotherapy (FIG. 22).

The invention claimed is:

1. A method for determining the effect of a compound on uptake of pathogens by host cells comprising:
   (a) labeling the pathogens with a detectable marker;
   (b) incubating a sample containing the host cells with the compound;
   (c) adding the labeled pathogens to the sample and incubating for a period of time sufficient for the labeled pathogen to enter the host cells;
   (d) lysing the host cells and collecting a lysate; and
   (e) determining a level of the pathogens internalized by the host cells by measuring the amount of label in the lysate; and
   (f) comparing the level of the pathogens internalized by the host cells with a level of pathogen internalized by the host cells in a control sample that did not contain the compound;
   wherein an increase in the level of pathogen internalized by the host cells in the sample relative to the level of pathogen internalized by the host cells in the control sample indicates the compound enhances uptake of the pathogen by the host cells, and a decrease in the level of pathogen internalized by the host cells in the sample relative to the level of pathogen internalized by the host cells in the control sample indicates the compound inhibits uptake of the pathogen by the host cells.

2. A method for identifying a host-targeting therapeutic comprising:
   (a) labeling pathogens with a detectable marker;
   (b) incubating a sample containing host cells with a compound suspected of being a host-target therapeutic;
   (c) adding the labeled pathogens to the sample and incubating for a period of time sufficient for the labeled pathogens to enter the host cells;
   (d) lysing the host cells and collecting a lysate; and
   (e) determining a level of the pathogens internalized by the host cells by measuring the amount of label in the lysate;
   (f) comparing the level of the pathogens internalized by the host cells with a level of pathogen internalized by the host cells in a control sample that did not contain the compound;

wherein an increase in the level of pathogen internalized by the host cells in the sample relative to the level of pathogen internalized by the host cells in the control sample indicates the compound enhances uptake of the pathogen by the host cells, and a decrease in the level of pathogen internalized by the host cells in the sample relative to the level of pathogen internalized by the host cells in the control sample indicates the compound inhibits uptake of the pathogen by the host cells.

3. The method of claim 1, wherein determining a level of the pathogens internalized by the host cells comprises: using the lysate to inoculate a media suitable for growth of the pathogen, incubating the media under conditions suitable for growth of the pathogen, measuring the amount of label at regular intervals, and determining the time it takes to initially detect the label.

4. The method of claim 1, further comprising determining the toxicity of the compound on the pathogen and/or the host cell.

5. The method of claim 1, further comprising incubating the host cells with the compound for a period of time sufficient to allow the compound to bind to the host cells or to affect one or more cellular processes of the host cells after step (b).

6. The method of claim 1, further comprising washing the host cells to remove compound(s) not associated with the host cells before adding the labeled pathogens and/or washing the host cells to remove pathogen that is not bound to or internalized by the host cells.

7. The method of claim 1, wherein the host cell comprises a macrophage.

8. The method of claim 7, wherein the macrophage comprises a primary macrophage and an immortalized culture macrophage cell.

9. The method of claim 8, wherein macrophage comprises a monocyte-derived macrophage (MDM), bone marrow-derived macrophage (BMDM), THP1 cell, or a RAW264.7 cell.

10. The method of claim 1, wherein labeling the pathogen with a detectable label comprises expressing a fluorescent protein in the pathogen.

11. The method of claim 1, wherein the pathogen is a bacterium.

12. The method of claim 11, wherein the pathogen is a gram-positive bacterium or a gram-negative bacterium.

13. The method of claim 1, wherein the pathogen is a virus.

* * * * *